(12) United States Patent
Linder et al.

(10) Patent No.: US 8,580,569 B2
(45) Date of Patent: Nov. 12, 2013

(54) FEEDBACK CONTROL IN MICROFLUIDIC SYSTEMS

(75) Inventors: Vincent Linder, Tewksbury, MA (US); David Steinmiller, Cambridge, MA (US)

(73) Assignee: OPKO Diagnostics, LLC, Woburn, MA (US)

( * ) Notice: Subject to any disclaimer, the term of this patent is extended or adjusted under 35 U.S.C. 154(b) by 204 days.

(21) Appl. No.: 13/088,112

(22) Filed: Apr. 15, 2011

(65) Prior Publication Data

US 2011/0253224 A1    Oct. 20, 2011

Related U.S. Application Data

(60) Provisional application No. 61/325,023, filed on Apr. 16, 2010, provisional application No. 61/325,044, filed on Apr. 16, 2010, provisional application No. 61/363,002, filed on Jul. 9, 2010.

(51) Int. Cl.
*G01N 35/08* (2006.01)

(52) U.S. Cl.
USPC ............ 436/55; 436/164; 436/172; 422/68.1; 422/82.08; 422/82.09; 700/266

(58) Field of Classification Search
None
See application file for complete search history.

(56) References Cited

U.S. PATENT DOCUMENTS

| | | | |
|---|---|---|---|
| 3,735,640 A | 5/1973 | Chizhov et al. | |
| 4,318,994 A | 3/1982 | Meyer et al. | |
| 4,517,302 A | 5/1985 | Saros | |
| 4,963,498 A | 10/1990 | Hillman et al. | |
| 5,051,237 A | 9/1991 | Grenner et al. | |
| 5,219,762 A | 6/1993 | Katamine et al. | |
| 5,268,147 A | 12/1993 | Zabetakis et al. | |

(Continued)

FOREIGN PATENT DOCUMENTS

| EP | 0 110 771 B1 | 3/1988 |
|---|---|---|
| EP | 0 643 307 A1 | 3/1995 |

(Continued)

OTHER PUBLICATIONS

Ahn, C. et al., "Disposable Smart Lab on a Chip for Point-of-Care Clinical Diagnostics", *Proceedings of the IEEE*, vol. 92, No. 1, pp. 154-173 (2004).

(Continued)

*Primary Examiner* — Robert Xu
(74) *Attorney, Agent, or Firm* — Wolf, Greenfield & Sacks, P.C.

(57) ABSTRACT

Systems and methods for controlling fluids in microfluidic systems are generally described. In some embodiments, control of fluids involves the use of feedback from one or more processes or events taking place in the microfluidic system. For instance, a detector may detect one or more fluids at a measurement zone of a microfluidic system and one or more signals, or a pattern of signals, may be generated corresponding to the fluid(s). In some cases, the signal or pattern of signals may correspond to an intensity, a duration, a position in time relative to a second position in time or relative to another process, and/or an average time period between events. Using this data, a control system may determine whether to modulate subsequent fluid flow in the microfluidic system. In some embodiments, these and other methods can be used to conduct quality control to determine abnormalities in operation of the microfluidic system.

36 Claims, 10 Drawing Sheets

(56) References Cited

U.S. PATENT DOCUMENTS

| | | | |
|---|---|---|---|
| 5,279,791 A | 1/1994 | Aldrich et al. | |
| 5,286,454 A | 2/1994 | Nilsson et al. | |
| 5,376,252 A | 12/1994 | Ekström et al. | |
| 5,478,751 A | 12/1995 | Oosta et al. | |
| 5,486,335 A | 1/1996 | Wilding et al. | |
| 5,571,410 A | 11/1996 | Swedberg et al. | |
| 5,635,358 A | 6/1997 | Wilding et al. | |
| 5,637,469 A | 6/1997 | Wilding et al. | |
| 5,726,026 A | 3/1998 | Wilding et al. | |
| 5,731,212 A | 3/1998 | Gavin et al. | |
| 5,866,345 A | 2/1999 | Wilding et al. | |
| 5,876,675 A | 3/1999 | Kennedy | |
| 5,932,799 A | 8/1999 | Moles | |
| 5,942,443 A | 8/1999 | Parce et al. | |
| 5,955,028 A | 9/1999 | Chow | |
| 5,957,579 A | 9/1999 | Kopf-Sill et al. | |
| 6,001,231 A | 12/1999 | Kopf-Sill | |
| 6,019,944 A | 2/2000 | Buechler | |
| 6,042,709 A | 3/2000 | Parce et al. | |
| 6,046,056 A | 4/2000 | Parce et al. | |
| 6,073,482 A | 6/2000 | Moles | |
| 6,103,199 A | 8/2000 | Bjornson et al. | |
| 6,114,122 A | 9/2000 | Besemer et al. | |
| 6,136,272 A | 10/2000 | Weigl et al. | |
| 6,146,489 A | 11/2000 | Wirth | |
| 6,146,589 A | 11/2000 | Chandler | |
| 6,168,948 B1 | 1/2001 | Anderson et al. | |
| 6,176,962 B1 | 1/2001 | Soane et al. | |
| 6,184,029 B1 | 2/2001 | Wilding et al. | |
| 6,186,660 B1 | 2/2001 | Kopf-Sill et al. | |
| 6,214,560 B1 | 4/2001 | Yguerabide et al. | |
| 6,238,538 B1 | 5/2001 | Parce et al. | |
| 6,241,560 B1 | 6/2001 | Furusawa et al. | |
| 6,251,343 B1 | 6/2001 | Dubrow et al. | |
| 6,274,337 B1 | 8/2001 | Parce et al. | |
| 6,293,012 B1 | 9/2001 | Moles | |
| 6,296,020 B1 | 10/2001 | McNeely et al. | |
| 6,331,439 B1 | 12/2001 | Cherukuri et al. | |
| 6,333,200 B1 | 12/2001 | Kaler et al. | |
| 6,353,475 B1 | 3/2002 | Jensen et al. | |
| 6,361,958 B1 | 3/2002 | Shieh et al. | |
| 6,413,782 B1 | 7/2002 | Parce et al. | |
| 6,416,642 B1 | 7/2002 | Alajoki et al. | |
| 6,429,025 B1 | 8/2002 | Parce et al. | |
| 6,432,720 B2 | 8/2002 | Chow | |
| 6,479,299 B1 | 11/2002 | Parce et al. | |
| 6,488,872 B1 | 12/2002 | Beebe et al. | |
| 6,488,894 B1 | 12/2002 | Miethe et al. | |
| 6,488,896 B2 | 12/2002 | Weigl et al. | |
| 6,495,104 B1 | 12/2002 | Unno et al. | |
| 6,551,841 B1 | 4/2003 | Wilding et al. | |
| 6,610,499 B1 | 8/2003 | Fulwyler et al. | |
| 6,613,512 B1 | 9/2003 | Kopf-Sill et al. | |
| 6,613,525 B2 | 9/2003 | Nelson et al. | |
| 6,620,625 B2 | 9/2003 | Wolk et al. | |
| 6,632,619 B1 | 10/2003 | Harrison et al. | |
| 6,638,482 B1 | 10/2003 | Ackley et al. | |
| 6,656,430 B2 | 12/2003 | Sheppard, Jr. et al. | |
| 6,656,431 B2 | 12/2003 | Holl et al. | |
| 6,669,831 B2 | 12/2003 | Chow et al. | |
| 6,705,357 B2 | 3/2004 | Jeon et al. | |
| 6,709,869 B2 | 3/2004 | Mian et al. | |
| 6,716,620 B2 | 4/2004 | Bashir et al. | |
| 6,742,661 B1 | 6/2004 | Schulte et al. | |
| 6,761,962 B2 | 7/2004 | Bentsen et al. | |
| 6,780,584 B1 | 8/2004 | Edman et al. | |
| 6,794,197 B1 | 9/2004 | Indermuhle et al. | |
| 6,818,184 B2 | 11/2004 | Fulwyler et al. | |
| 6,827,095 B2 | 12/2004 | O'Connor et al. | |
| 6,828,143 B1 | 12/2004 | Bard | |
| 6,830,936 B2 | 12/2004 | Anderson et al. | |
| 6,858,185 B1 | 2/2005 | Kopf-Sill et al. | |
| 6,878,271 B2 | 4/2005 | Gilbert et al. | |
| 6,878,755 B2 | 4/2005 | Singh et al. | |
| 6,919,045 B1 | 7/2005 | Berndt | |
| 6,949,377 B2 | 9/2005 | Ho | |
| 6,953,550 B2 | 10/2005 | Sheppard, Jr. et al. | |
| 6,987,263 B2 | 1/2006 | Hobbs et al. | |
| 6,989,128 B2 | 1/2006 | Alajoki et al. | |
| 7,005,292 B2 | 2/2006 | Wilding et al. | |
| 7,010,391 B2 * | 3/2006 | Handique et al. | 700/266 |
| 7,015,046 B2 | 3/2006 | Wohlstadter et al. | |
| 7,018,830 B2 | 3/2006 | Wilding et al. | |
| 7,067,263 B2 | 6/2006 | Parce et al. | |
| 7,087,148 B1 | 8/2006 | Blackburn et al. | |
| 7,091,048 B2 | 8/2006 | Parce et al. | |
| 2001/0027918 A1 | 10/2001 | Parce et al. | |
| 2002/0001818 A1 | 1/2002 | Brock | |
| 2002/0019059 A1 | 2/2002 | Chow et al. | |
| 2002/0071788 A1 | 6/2002 | Fujii et al. | |
| 2002/0092767 A1 | 7/2002 | Bjornson et al. | |
| 2002/0142618 A1 | 10/2002 | Parce et al. | |
| 2002/0199094 A1 | 12/2002 | Strand et al. | |
| 2003/0012697 A1 | 1/2003 | Hahn et al. | |
| 2003/0082081 A1 | 5/2003 | Fouillet et al. | |
| 2003/0118486 A1 | 6/2003 | Zhou et al. | |
| 2003/0124623 A1 | 7/2003 | Yager et al. | |
| 2003/0138969 A1 | 7/2003 | Jakobsen et al. | |
| 2003/0207328 A1 | 11/2003 | Yguerabide et al. | |
| 2004/0077074 A1 | 4/2004 | Ackley et al. | |
| 2004/0115094 A1 | 6/2004 | Gumbrecht et al. | |
| 2004/0228771 A1 | 11/2004 | Zhou et al. | |
| 2005/0014248 A1 | 1/2005 | Canton | |
| 2005/0118073 A1 | 6/2005 | Facer et al. | |
| 2005/0161669 A1 | 7/2005 | Jovanovich et al. | |
| 2005/0221281 A1 | 10/2005 | Ho | |
| 2005/0238545 A1 | 10/2005 | Parce et al. | |
| 2005/0243304 A1 | 11/2005 | Padmanabhan et al. | |
| 2005/0255003 A1 | 11/2005 | Summersgill et al. | |
| 2006/0002827 A1 | 1/2006 | Curcio et al. | |
| 2006/0046300 A1 * | 3/2006 | Padmanabhan et al. | 436/55 |
| 2006/0076482 A1 | 4/2006 | Hobbs et al. | |
| 2006/0094119 A1 | 5/2006 | Ismagilov et al. | |
| 2006/0202133 A1 | 9/2006 | Ok et al. | |
| 2006/0257992 A1 | 11/2006 | McDevitt et al. | |
| 2006/0275852 A1 | 12/2006 | Montagu | |
| 2007/0003434 A1 | 1/2007 | Padmanabhan et al. | |
| 2007/0009386 A1 | 1/2007 | Padmanabhan et al. | |
| 2007/0031289 A1 | 2/2007 | Cox et al. | |
| 2007/0048189 A1 | 3/2007 | Cox et al. | |
| 2007/0120903 A1 | 5/2007 | Takagi | |
| 2007/0166195 A1 | 7/2007 | Padmanabhan et al. | |
| 2007/0172388 A1 | 7/2007 | Padmanabhan et al. | |
| 2007/0298433 A1 | 12/2007 | Sia et al. | |
| 2008/0085219 A1 | 4/2008 | Beebe et al. | |
| 2008/0107565 A1 | 5/2008 | Vivienne et al. | |
| 2008/0248590 A1 | 10/2008 | Gulliksen et al. | |
| 2009/0022625 A1 | 1/2009 | Lee et al. | |
| 2009/0156966 A1 | 6/2009 | Kontschieder et al. | |
| 2010/0027008 A1 | 2/2010 | Bornhop et al. | |

FOREIGN PATENT DOCUMENTS

| | | |
|---|---|---|
| EP | 1 054 259 A1 | 11/2000 |
| EP | 1 898 210 A2 | 3/2008 |
| EP | 1946830 A1 | 7/2008 |
| EP | 2071026 A1 | 6/2009 |
| WO | WO 91/01003 A | 1/1991 |
| WO | WO 02/22250 A2 | 3/2002 |
| WO | WO 03/054513 A2 | 7/2003 |
| WO | WO 2004/087951 A3 | 10/2004 |
| WO | WO 2005056186 A1 | 6/2005 |
| WO | WO 2005/072858 | 8/2005 |
| WO | WO 2006018044 A1 | 2/2006 |
| WO | WO 2006/056787 A1 | 6/2006 |
| WO | WO 2006/103440 A2 | 10/2006 |
| WO | WO 2006113727 A2 | 10/2006 |
| WO | WO 2007/082480 A1 | 7/2007 |
| WO | WO 2008/028124 A1 | 3/2008 |
| WO | WO 2008/118098 A1 | 10/2008 |
| WO | WO 2008/123112 A1 | 10/2008 |

(56) References Cited

FOREIGN PATENT DOCUMENTS

OTHER PUBLICATIONS

Andersson, et al., "Micromachined flow-through filter-chamber for chemical reactions on beads", *Sensors and Actuators*, vol. B67, pp. 203-208 (2000).

Atencia, J et al., "Capillary inserts in microcirculatory systems", *Lab Chip*, 6, 575-577 (2006).

Atencia, J. et al. "Steady flow generation in microcirculatory systems", *Lab Chip*, 6, 567-574 (2006).

Daridon, et al., "Chemical sensing using an integrated microfluidic system based on the Berthelot reaction", *Sensors and Actuators B*, vol. 76, pp. 235-243 (2001).

Dodge, et al., "Electrokinetically Driven Microfluidic Chips with Surface-Modified Chambers for Heterogeneous Immunoassays", *Anal. Chem.*, vol. 73, pp. 3400-3409 (2001).

Fredrickson, C. et al., "Macro-to-micro interfaces for microfluidic devices", *Lab Chip*, 4, 526-533 (2004).

Grodzinski, P. et al., "A Modular Microfluidic System for Cell Pre-concentration and Genetic Sample Preparation", *Biomedical Microdevices*, 5:4,303-310 (2003).

Juncker, et al., "Autonomous Microfluidic Capillary Systems", *Anal. Chem*, vol. 74, pp. 6139-6144 (2002).

Linder, et al., "Reagent-Loaded Cartridges for Valveless and Automated Fluid Delivery in Microfluidic Devices", *Anal Chem.*, vol. 77, No. 1, pp. 64-71 (2005).

Moorthy, et al., "Microfluidic tectonics platform: A colorimetric, disposable botulinum toxin enzyme-linked immunosorbent assay system", Electrophoresis, vol. 25, pp. 1705-1713 (2004).

Obeid, et al., "Microfabricated Device for DNA and RNA Amplification by Continuous-Flow Polymerase Chain Reaction and Reverse Transcription-Polymerase Chain Reaction with Cycle Number Selection", *Anal. Chem.*, vol. 75, pp. 288-295 (2003).

Sia, S., et al., "An Integrated Approach to a Portable and Low-Cost Immunoassay for Resource-Poor Settings", *Angew. Chem. Int. Ed.*, vol. 43, pp. 498-502 (2004).

Sia, S., et al., "Microfluidic devices fabricated in poly(dimethlysiloxane) for biological studies", *Electrophoresis*, vol. 24, pp. 3563-3576 (2003).

Song et al., "A microfluidic system for controlling reaction networks in time", *Angew. Chem. Int. Ed.*, vol. 42, No. 7, 768-772 (2003).

Weigl, et al., "Lab-on-a-chip for drug development", *Advanced Drug Delivery Reviews*, vol. 55, pp. 349-377 (2003).

Proceedings of uTAS 2004, 8th International Conference on Miniaturized Systems in Chemistry and Life Sciences, Sep. 26-30, Malmo, Sweden, Edited by Thomas Laurell, Johan Nilsson, Klavs Jensen, D. Jed Harrison, Jorg P. Kutter, The Royal Society of Chemistry, pp. 1-135 (2004).

International Search Report and Written Opinion dated Sep. 23, 2011 from PCT/US2011/032680.

International Search Report and Written Opinion dated Sep. 23, 2011 from PCT/US2011/032685.

\* cited by examiner

FEEDBACK CONTROL IN MICROFLUIDIC SYSTEMS

RELATED APPLICATIONS

The present application claims priority to U.S. provisional applications U.S. Ser. No. 61/325,023, filed Apr. 16, 2010, U.S. Ser. No. 61/325,044, filed Apr. 16, 2010, and U.S. Ser. No. 61/363,002, filed Jul. 9, 2010, each of which is incorporated herein by reference in its entirety.

FIELD

Systems and methods for controlling fluids in microfluidic systems are generally described. In some embodiments, control of fluids involves the use of feedback from one or more processes or events taking place in the microfluidic system.

BACKGROUND

The manipulation of fluids plays an important role in fields such as chemistry, microbiology and biochemistry. These fluids may include liquids or gases and may provide reagents, solvents, reactants, or rinses to chemical or biological processes. While various microfluidic methods and devices, such as microfluidic assays, can provide inexpensive, sensitive and accurate analytical platforms, fluid manipulations—such as the mixture of multiple fluids, sample introduction, introduction of reagents, storage of reagents, separation of fluids, collection of waste, extraction of fluids for off-chip analysis, and transfer of fluids from one chip to the next—can add a level of cost and sophistication. Accordingly, advances in the field that could reduce costs, simplify use, provide quality control of the analysis being performed, and/or improve fluid manipulations in microfluidic systems would be beneficial.

SUMMARY

Systems and methods for controlling fluids in microfluidic systems are generally described. In some embodiments, control of fluids involves the use of feedback from one or more processes or events taking place in the microfluidic system. The subject matter of the present invention involves, in some cases, interrelated products, alternative solutions to a particular problem, and/or a plurality of different uses of one or more systems and/or articles.

In one set of embodiments, a series of methods are provided. In one embodiment, a method comprises initiating detection of fluids at a first measurement zone of a microfluidic system. The method involves detecting a first fluid and a second fluid at the first measurement zone and forming a first signal corresponding to the first fluid and a second signal corresponding to the second fluid. A first pattern of signals is transmitted to a control system, the first pattern of signals comprising at least two of: a) an intensity of the first signal; b) a duration of the first signal; c) a position of the first signal in time relative to a second position in time; and d) an average time period between the first and second signals. The method also involves determining whether to modulate fluid flow in the microfluidic system based at least in part on the first pattern of signals.

In another embodiment, a method comprises detecting a first fluid and a second fluid at a first measurement zone of a microfluidic system, wherein the detection step comprises detecting at least two of a) an opacity of the first fluid; b) a volume of the first fluid; c) a flow rate of the first fluid; d) a position of the detection of the first fluid in time relative to a second position in time; and e) an average time period between the detection of the first and second fluids. The method involves determining whether to modulate fluid flow in the microfluidic system based at least in part on the detection step.

In another embodiment, a method of conducting quality control to determine abnormalities in operation of a microfluidic system comprises detecting a first fluid at a first measurement zone of the microfluidic system and forming a first signal corresponding to the first fluid. The method also involves transmitting the first signal to a control system, comparing the first signal to a reference signal, thereby determining the presence of abnormalities in operation of the microfluidic system, and determining whether to stop an analysis being conducted in the microfluidic system based at least in part on results of the comparing step.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1:
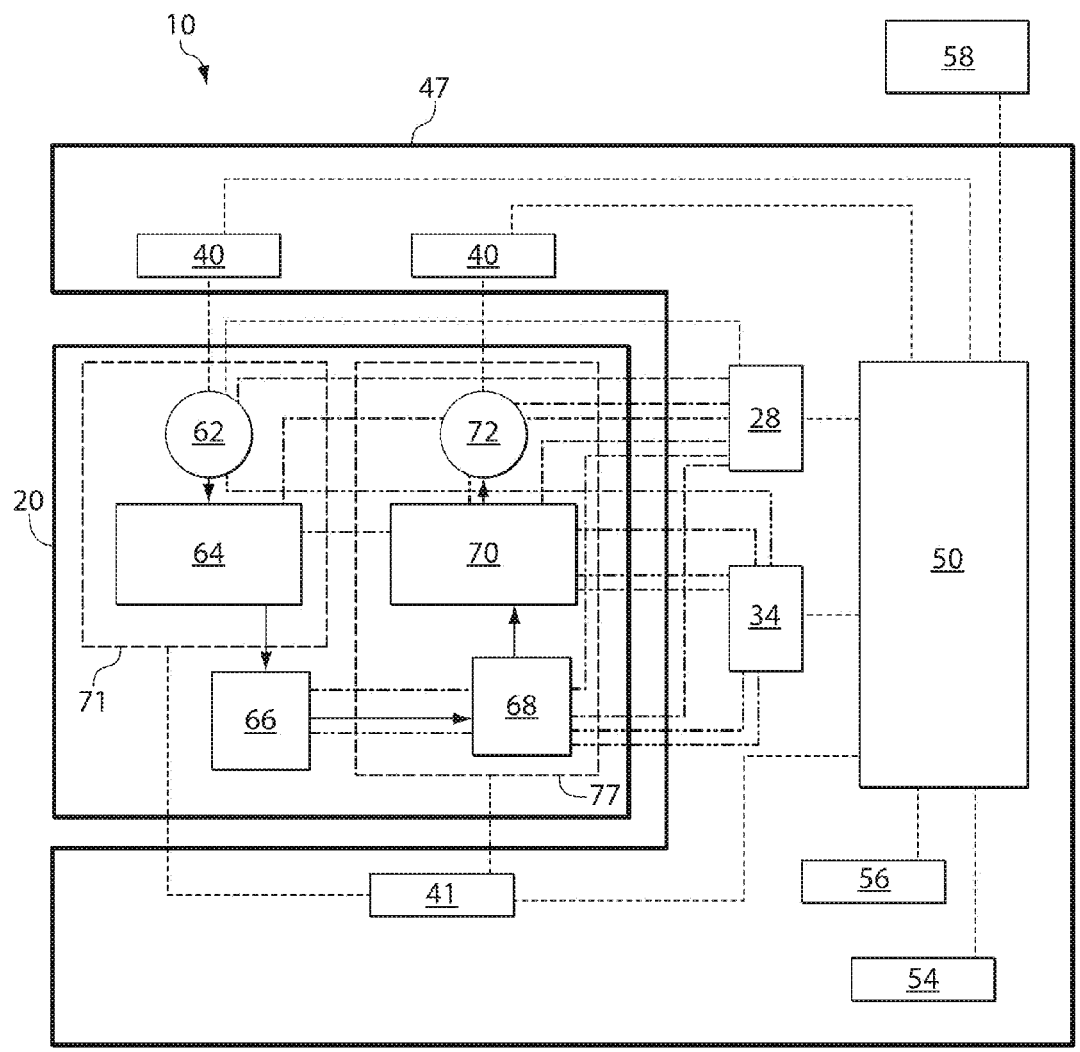
FIG. 1 is a block diagram showing a microfluidic system and a variety of components that may be part of a sample analyzer according to one embodiment.

Systems and methods for controlling fluids in microfluidic systems are generally described. In some embodiments, control of fluids involves the use of feedback from one or more processes or events taking place in the microfluidic system. For instance, a detector may detect one or more fluids passing across a measurement zone of a microfluidic system and one or more signals, or a pattern of signals, may be generated corresponding to the fluid(s). In some cases, the signal or pattern of signals may correspond to an intensity (e.g., an indication of the type of fluid passing across the detector), a duration (e.g., an indication of the volume and/or flow rate of fluid), a position in time relative to another position in time or relative to another process that has occurred in the microfluidic system (e.g., when a certain fluid passes across the detector after a valve has been actuated), and/or an average time period between events (e.g., between two consecutive signals). Using this data, a control system may determine whether to modulate subsequent fluid flow in the microfluidic system. In some embodiments, these and other methods can be used to conduct quality control to determine abnormalities in operation of the microfluidic system.

As described in more detail below, in some embodiments an analysis performed in a device can be recorded to produce essentially a "fingerprint" of the analysis, and all or potions of the fingerprint may be used to provide feedback to the microfluidic system. For example, a fingerprint of an analysis may include signals from each fluid at (e.g., passing across, through, above, below, etc.) a detector or multiple detectors, which may be statically positioned at a measurement zone or at multiple measurement zones of a device. The signals may be a measurement of, for example, the transmission of light passing through the fluids. Since different fluids used in the analysis may have different volumes, flow rates, compositions, and other characteristics, the fluids may produce signals having different intensities and durations, which are reflected in the fingerprint. As such, the fingerprint can be used to identify, for example, the fluids used in the analysis, the timing of the fluids (e.g., when particular fluids were introduced into certain regions of the device), and the interaction between the fluids (e.g., mixing). This data can be used to provide feedback to modulate subsequent fluid flow in the microfluidic system, and in some cases, to conduct quality control to determine whether all or portions of the analysis was run properly.

The systems and methods described herein may find application in a variety of fields. In some cases, the systems and methods may be used to conduct quality control to determine, for example, a correct sequence of events taking place in the microfluidic system. If an incorrect sequence of events is determined, the feedback control may, for example, cancel the test being performed in the microfluidic system and/or alert the user of the abnormality. Additionally and/or alternatively, the systems and methods described herein may be used to modulate fluid flow such as mixing, introduction or removal of fluids into certain channels or reservoirs in the microfluidic system, actuation of one or more components such as a valve, pump, vacuum, or heater, and other processes. These and other processes may be applied to a variety of microfluidic systems such as, for example, microfluidic point-of-care diagnostic platforms, microfluidic laboratory chemical analysis systems, high-throughput detection systems, fluidic control systems in cell cultures or bio-reactors, among others. The articles, systems, and methods described herein may be particularly useful, in some cases, where an inexpensive, robust, disposable microfluidic device is desired.

Furthermore, the feedback control described herein may be used to perform any suitable process in a microfluidic system, such as a chemical and/or biological reaction. As a specific example, the feedback control may be used to control reagent transport in antibody assays that employ unstable reaction precursors, such as the silver solution assay described in the Examples section. Other advantages are described in more detail below.

The articles, components, systems, and methods described herein may be combined with those described in International Patent Publication No. WO2005/066613 (International Patent Application Serial No. PCT/US2004/043585), filed Dec. 20, 2004 and entitled "Assay Device and Method"; International Patent Publication No. WO2005/072858 (International Patent Application Serial No. PCT/US2005/003514), filed Jan. 26, 2005 and entitled "Fluid Delivery System and Method"; International Patent Publication No. WO2006/113727 (International Patent Application Serial No. PCT/US06/14583), filed Apr. 19, 2006 and entitled "Fluidic Structures Including Meandering and Wide Channels"; U.S. patent application Ser. No. 12/113,503, published as U.S. Patent Publication No. 2008/0273918, filed May 1, 2008 and entitled "Fluidic Connectors and Microfluidic Systems"; U.S. patent application Ser. No. 12/196,392, published as U.S. Patent Publication No. 2009/0075390, filed Aug. 22, 2008, entitled "Liquid containment for integrated assays"; U.S. patent application Ser. No. 12/428,372, filed Apr. 22, 2009, published as U.S. Patent Publication No. 2009/0266421, entitled "Flow Control in Microfluidic Systems"; U.S. patent application Ser. No. 12/640,420, filed Dec. 17, 2009, entitled, "Reagent Storage in Microfluidic Systems and Related Articles and Methods"; U.S. patent application Ser. No. 12/698,451, filed Feb. 2, 2010, entitled, "Structures for Controlling Light Interaction with Microfluidic Devices"; U.S. Patent Apl. Ser. No. 61/263,981, filed Nov. 14, 2009 and entitled, "Fluid Mixing and Delivery in Microfluidic Systems; U.S. Provisional Patent Application No. 61/325,044, filed Apr. 16, 2010 and entitled, "System for Analysis of Samples", each of which is incorporated herein by reference in its entirety for all purposes.

A series of exemplary systems and methods are now described.

FIG. 1 shows a block diagram 10 of a microfluidic system and various components that may provide feedback control according to one set of embodiments. The microfluidic system may include, for example, a device or cassette 20 operatively associated with one or more components such as a fluid flow source 40 such as a pump (e.g., for introducing one or more fluids into the device and/or for controlling the rates of fluid flow), optionally a fluid flow source 40 such as a pump or vacuum that may be configured to apply either of both of a positive pressure or vacuum (e.g., for moving/removing one or more fluids within/from the cassette and/or for controlling the rates of fluid flow), a valving system 28 (e.g., for actuating one or more valves), a detection system 34 (e.g., for detecting one or more fluids and/or processes), and/or a temperature regulating system 41 (e.g., to heat and/or cool one or more regions of the device). The components may be external or internal to the microfluidic device, and may optionally include one or more processors for controlling the component or system of components. In certain embodiments, one or more such components and/or processors are associated with a sample analyzer 47 configured to process and/or analyze a sample contained in the microfluidic system. Non-limiting examples of analyzers that may be used with microfluidic systems and devices described herein are described in more detail below and in U.S. Provisional Patent Application No. 61/325,044, filed Apr. 16, 2010 and entitled, "System for Analysis of Samples", which is incorporated herein by reference in its entirety for all purposes.

In general, as used herein, a component that is "operatively associated with" one or more other components indicates that such components are directly connected to each other, in direct physical contact with each other without being connected or attached to each other, or are not directly connected to each other or in contact with each other, but are mechanically, electrically (including via electromagnetic signals transmitted through space), or fluidically interconnected (e.g., via channels such as tubing) so as to cause or enable the components so associated to perform their intended functionality.

The components shown illustratively in FIG. 1, as well as other optional components, may be operatively associated with a control system 50. In some embodiments, the control system may be used to control fluids and/or conduct quality control by the use of feedback from one or more events taking place in the microfluidic system. For instance, the control system may be configured to receive input signals from the one or more components, to calculate and/or control various parameters, to compare one or more signals or a pattern of signals with signals or values pre-programmed into the control system, and/or to send signals to one or more components to modulate fluid flow and/or control operation of the microfluidic system. Specific examples of feedback control are provided below.

The control system may also be optionally associated with other components such as a user interface 54, an identification system 56, an external communication unit 58 (e.g., a USB), and/or other components, as described in more detail below.

Microfluidic device (e.g., cassette) 20 may have any suitable configuration of channels and/or components for performing a desired analysis. In one set of embodiments, microfluidic device 20 contains stored reagents that can be used for performing a chemical and/or biological reaction (e.g., an immunoassay). The microfluidic device may include, for example, an optional reagent inlet 62 in fluid communication with an optional reagent storage area 64. The storage area may include, for example, one or more channels and/or reservoirs that may, in some embodiments, be partially or completely filled with fluids (e.g., liquids and gases, including immiscible reagents such as reagent solutions and wash solutions, optionally separated by immiscible fluids, as described in more detail below). The device may also include an optional sample or reagent loading area 66, such as a fluidic connector that can be used to connect reagent storage area 64 to an optional measurement zone 68 (e.g., a reaction area). Examples of fluidic connectors are described in more detail in U.S. patent application Ser. No. 12/113,503, published as U.S. Patent Publication No. 2008/0273918, filed May 1, 2008 and entitled "Fluidic Connectors and Microfluidic Systems", which is incorporated herein by reference in its entirety. The measurement zone, which may include one or more zones (e.g., detection regions) for detecting a component in a sample, may be in fluid communication with an optional waste area 70 and coupled to outlet 72. In one set of embodiments, fluid may flow in the direction of the arrows shown in the figure. Further description and examples of such and other components are provided in more detail below.

In some embodiments, sections 71 and 77 of the device are not in fluid communication with one another prior to introduction of a sample into the device. In some cases, sections 71 and 77 are not in fluid communication with one another prior to first use of the device, wherein at first use, the sections are brought into fluid communication with one another. In other embodiments, however, sections 71 and 77 are in fluid communication with one another prior to first use and/or prior to introduction of a sample into the device. Other configurations of devices are also possible.

As shown in the exemplary embodiment illustrated in FIG. 1, one or more fluid flow sources 40 such as a pump and/or a vacuum or other pressure-control system, valving system 28, detection system 34, temperature regulating system 41, and/or other components may be operatively associated with one or more of reagent inlet 62, reagent storage area 64, sample or reagent loading area 66, measurement zone 68, waste area 70, outlet 72, and/or other regions of microfluidic device 20. Detection of processes or events in one or more regions of the microfluidic device can produce a signal or pattern of signals that can be transmitted to control system 50. Based (at least in part) on the signal(s) received by the control system, this feedback can be used to manipulate fluids within and/or between each of these regions of the microfluidic device, such as by controlling one or more of a pump, vacuum, valving system, detection system, temperature regulating system, and/or other components. In some cases, the feedback can determine abnormalities that have occurred in the microfluidic system, and the control system may send a signal to one or more components to cause all or portions of the system to shut down. Consequently, the quality of the processes being performed in the microfluidic system can be controlled using the systems and methods described herein.

In some embodiments, feedback control involves the detection of one or more events or processes occurring in a microfluidic system. A variety of detection methods can be used, as described in more detail below. Detection may involve, for example, determination of at least one characteristic of a fluid, a component within a fluid, interaction between components within regions of the microfluidic device, or a condition within a region of the microfluidic device (e.g., temperature, pressure, humidity). For instance, detection may involve detecting an opacity of one or more fluids, a concentration of one or more components in a fluid, a volume of one or more fluids, a flow rate of one or more fluids, a position of detecting a first fluid in time relative to a second position in time, and an average time period between the detection of a first fluid and a second fluid. Detection of the one more characteristics, conditions, or events may, in some embodiments, result in the generation of one or more signals, which can be optionally further processed and transmitted to the control system. As described in more detail herein, the one or more signals may be compared with one or more signals, values or thresholds pre-programmed into the control system, and may be used to provide feedback to the microfluidic system.

A variety of signals or patterns of signals can be generated and/or determined (e.g., measured) using the systems and methods described herein. In one set of embodiments, a signal includes an intensity component. Intensity may indicate or be used to indicate, for example, one or more of: the concentration of a component in a fluid, an indication of the type of fluid being detected (e.g., a sample type such as blood versus urine, or a physical characteristic of the fluid such as a liquid versus a gas), the amount of a component in a fluid, and the volume of a fluid. In some cases, intensity is determined by an opacity of a fluid or a component. In other embodiments, intensity is determined by the use of a marker or label such as a fluorescent marker or label.

In some embodiments, a frequency of signals may be generated and/or determined For example, a series of signals each having an intensity (e.g., above or below a threshold intensity) may be measured by a detector. This number may be compared with a number of signals or values (having the intensity above or below the threshold intensity) pre-programmed into a control system or other unit. Based at least in part on this comparison, the control system may initiate, halt, or change a condition such as the modulation of fluid flow in the microfluidic system.

In some embodiments, a duration of a signal is generated and/or determined The duration of a signal may indicate or be used to indicate, for example, one or more of: the volume of a fluid, the flow rate of a fluid, a characteristic of a component within a fluid (e.g., how long a component has a certain activity, such as chemiluminescence, fluorescence, and the like), and how long a particular fluid has been positioned in a specific region of the microfluidic device.

In some embodiments, a position of a signal in time relative to a second position in time or relative to another process or event (e.g., that has occurred in the microfluidic system) is generated and/or determined For example, a detector may detect when a certain fluid passes across the detector (e.g., a first position in time), and the timing of this signal may be related to a second position in time (e.g., when detection was initiated; a certain amount of time after a process has occurred, etc.). In another example, a detector may detect when a certain fluid passes across the detector after (or before) a component of the microfluidic system (e.g., a valve) has been actuated. In one embodiment, the opening of a valve may indicate that the mixing of reagents is about to occur, and thus the position of the signal in time may give some indication of when a certain fluid passes across the detector after (or before) the mixing of the reagents. If the position of the signal of the fluid occurs within a certain time range after (or before) the mixing of reagents, for example, this may indicate that the analysis is running properly.

In another example, a detector may detect when a second fluid passes across the detector after a first fluid has passed across the detector. In other embodiments, a position of a signal in time is determined relative to a certain event or process that is taking or has taken place in the microfluidic system (e.g., the start of the analysis, the initiation of fluid flow, the initiation of detection in the microfluidic system, upon a user inserting the microfluidic device into an analyzer, etc.).

In another set of embodiments, an average time between signals or events is generated and/or determined. For instance, the average time period between two signals may be measured, where each of the signals may independently correspond to one or more characteristics or conditions described herein. In other embodiments, the average time between the first and the last of a series of similar signals is determined (e.g., the average time between a series of wash fluids passing across a detector).

In certain embodiments, a pattern of signals is generated and/or determined. The pattern of signals may include, for example, at least two of (or, in other embodiments, at least three of, or at least four of) an intensity of a signal, a frequency of signals, a duration of a signal, a position of a signal in time relative to a second position in time or relative to another process or event occurring (or has occurred) in the microfluidic system, and an average time period between two or more signals or events. In other embodiments, the pattern of signals comprises at least two of (or, in other embodiments, at least three of, or at least four of) an intensity of a first signal, a duration of the first signal, a position of the first signal in time relative to a second position in time; an intensity of a second signal, a duration of the second signal, a position of the second signal in time relative to a second position in time, and an average time period between the first and second signals. The pattern of signals may indicate, in some embodiments, whether a particular event or process is taking place properly within the microfluidic system. In other embodiments, the pattern of signals indicates whether a particular process or event has occurred in the microfluidic system. In yet other embodiments, a pattern of signals can indicate a particular sequence of events.

A variety of signals or patterns of signals, such as those described above and herein, can be generated and/or determined and can be used alone or in combination to provide feedback for controlling one more or more processes, such as modulation of fluid flow in a microfluidic system. That is, the control system or any other suitable unit may determine, in some embodiments, whether to modulate fluid flow in the microfluidic system based at least in part on the pattern of signals. For example, determination of whether to modulate fluid flow based at least in part on a pattern of signals that includes an intensity of a first signal and a position in time of the first signal relative to a second position in time may involve the use of both of these pieces of information to make a decision on whether or not to modulate fluid flow. For instance, these signals may be compared to one or more reference signals (e.g., a threshold intensity or intensity range, and a threshold position in time or range of positions in time, relative to a second position in time) that may be pre-programmed or pre-set into the control system. If each of the measured signals falls within the respective threshold values or ranges, a decision on whether to modulate fluid flow can be made. Only one of the parameters to be considered (e.g., only an intensity of the first signal or only a position in time of the first signal) that meets a threshold value or range may not be sufficient information to make a decision on whether or not to modulate fluid flow, because it may not give enough information about the fluid(s) or component(s) that gave rise to the signal(s) for the purposes described herein. For example, in some cases the fluid or component detected may not be sufficiently identified for the purposes described herein unless a pattern of signals is taken into consideration.

In certain embodiments, one or more measured signals is processed or manipulated (e.g., before or after transmission, and/or before being compared to a reference signal or value). It should be appreciated, therefore, that when a signal is transmitted (e.g., to a control system), compared (e.g., with a reference signal or value), or otherwise used in a feedback process, that the raw signal may be used or a processed/manipulated signal based (at least in part) on the raw signal may be used. For example, in some cases, one or more derivative signals of a measured signal can be calculated (e.g., using a differentiator, or any other suitable method) and used to provide feedback. In other cases, signals are normalized (e.g., subtracting a measured signal from a background signal). In one set of embodiments, a signal comprises a slope or average slope, e.g., an average slope of intensity as a function of time.

In some cases, the measured signal may be converted to a digital signal with the use of an analog to digital converter so that all further signal processing may be performed by a digital computer or digital signal processor. Although in one embodiment, all signal processing is performed digitally, the present invention is not so limited, as analog processing techniques may alternatively be used. For instance, a digital to analog converter may be used to produce an output signal. Signals may be processed in a time domain (one-dimensional signals), spatial domain (multidimensional signals), frequency domain, autocorrelation domain, or any other suitable domain. In some cases, signals are filtered, e.g., using a linear filter (a linear transformation of a measured signal), a non-linear filter, a causal filter, a non-causal filter, a time-invariant filter, a time-variant filter, or other suitable filters. It should be understood that the signals, patterns, and their use in feedback described herein are exemplary and that the invention is not limited in this respect.

Once a signal or pattern of signals has been determined, the signal(s) may be optionally transmitted to a control system. In some cases, the control system compares the signal or pattern of signals to a second set of signal(s). The second signal or pattern of signals may be, for example, signal(s) determined previously in the microfluidic system, or reference signal(s) or value(s) which may have been pre-programmed into the control system or other unit of the microfluidic system. In some cases, a reference signal or pattern of signals includes one or more threshold values or a range of threshold values. The control system may compare a first signal or pattern of signals with a second signal or pattern of signals (e.g., reference signals), and determine whether to initiate, cease, or modulate one or more events or series of events in the microfluidic system. That is, the measured signal or pattern of signals can be used by the control system to generate a drive signal and provide feedback control to the microfluidic system. For example, the control system may determine whether to modulate fluid flow (e.g., flow rate, mixing, the ceasing of flow of one or more fluids) in one or more regions of the microfluidic system. Other conditions such a modulation of temperature, pressure, humidity, or other conditions can also be controlled. This modulation may be performed, in certain embodiments, by the control system sending one or more drive signals to an appropriate component of the microfluidic system (e.g., a valve, pump, vacuum, heater, or other component) to actuate that or another component. Any suitable valve drive electronics circuit may be used to receive a drive signal and convert the drive signal to a voltage, current, or other signal capable of actuating the component. In certain embodiments, the control system can determine whether or not to cease operation of one or more components of the microfluidic system. In some cases, the control system may determine whether or not to stop an analysis or a portion of an analysis being conducted in the microfluidic system.

In some embodiments, a method of conducting feedback control may involve initiating detection of fluids at a first measurement zone of a microfluidic system. A first fluid and a second fluid may be detected at the first measurement zone and a first signal corresponding to the first fluid and a second signal corresponding to the second fluid may be formed. A first pattern of signals may be transmitted to a control system, the first pattern of signals comprising at least two of an intensity of the first signal, a duration of the first signal, a position of the first signal in time relative to a second position in time, and an average time period between the first and second signals. A decision about whether to modulate fluid flow in the microfluidic system may be determined based at least in part on the first pattern of signals.

It should be understood that while much of the description herein describes the use of signals or patterns of signals, the invention is not so limited and that aspects of feedback control or other processes involving determination of characteristics, conditions or events involving fluids or components may not require the generation, determination (e.g., measurement) or analysis of signals or patterns of signals in some embodiments.

In some embodiments, a method of conducting feedback involves detecting a first fluid and a second fluid at a first measurement zone of a microfluidic system, wherein the detection step comprises detecting at least two of (or at least three of) an opacity of the first fluid, a volume of the first fluid, a flow rate of the first fluid, a position of the detection of the first fluid in time relative to a second position in time, and an average time period between the detection of the first and second fluids. A decision about whether to modulate fluid flow in the microfluidic system may be determined based at least in part on the detection step.

In some embodiments, feedback control can be used to modulate the same condition, event, or type of condition or event that was first detected. For instance, the concentration of a component in a fluid can be determined, and a signal can be generated and transmitted to a control system, which determines whether or not the concentration of the same component should be increased or decreased in the region of the microfluidic device. In another example, the flow rate of a fluid in a channel is measured, and based at least in part on the signal generated from the measurement, the source of fluid flow (e.g., a vacuum or pump) or a valve is used to modulate the flow rate in that same channel. In such and other embodiments, the signal generated may be compared to a pre-determined signal or values indicating a desired value or range of conditions (e.g., concentration, flow rate). The feedback control may involve a feedback loop (e.g., a positive or negative feedback loop) in some cases. In other cases, feedback control does not involve a feedback loop.

In other embodiments, however, (including many of the examples described herein) feedback control is based at least in part on the determination of one or more first conditions or events taking place in the microfluidic system, and signals from the one or more conditions or events is used to control a second, different set of conditions or events taking place (or events that will take place) in the microfluidic system. In certain embodiments, the second, different set of conditions or events do not substantially affect the first set of conditions or events (e.g., in contrast to the examples of above involving the modulation of concentration of a component or the flow rate in a channel). In some cases, detection takes place at a measurement zone, and feedback from the measurement zone is used to modulate fluid flow at a different region of the microfluidic system. For example, detection of a certain fluid passing across a detection system may trigger control of whether or not a particular valve is actuated to allow flow of one or more different fluids in a different region of the microfluidic system. In one particular embodiment, detection of a first fluid at (e.g., passing across) a reaction area may trigger the mixing of second and third fluids at a mixing region of the microfluidic system. The second and third fluids may be initially positioned at a different region (e.g., a storage region) of the microfluidic system than from where detection and production of the signal used to provide feedback takes place. In another example, the measurement of optical density of a sample flowing across a measurement zone (e.g., a first condition) gives an indication of whether the sample was introduced at the right time and/or the presence of the correct type or volume of sample. The one or more signals from this measurement can be compared to one or more pre-set values, and based (at least in part) on this feedback and comparison, a control system may cease fluid flow in the microfluidic system (e.g., a second, different condition) if the measured signals falls out of range with the pre-set values. In some such and other embodiments, the first condition or event has already passed after the detection step, such that feedback control does not substantially modulate that same condition, event, or type of condition or event that produced the signal used for feedback.

In some embodiments, one or more feedback control methods such as proportional control, integral control, proportional-integral control, derivative control, proportional-derivative control, integral-derivative control, and proportional-integral-derivative control can be used by a control system to modulate fluid flow. The feedback control may involve a feedback loop in some embodiments. In some cases involving one or more of the aforementioned feedback control methods, a drive signal (which may be used to modulate fluid flow, e.g., by actuating a component of the microfluidic system) may be generated based at least in part on a signal that is the difference between a pre-programmed threshold signal or value (which may be indicative of a future action to be performed) and a feedback signal that is measured by a detector.

Detection of a condition or an event taking place in a microfluidic system may have a variety of forms. In some cases, detection occurs continuously. In other embodiments, detection occurs periodically; and yet other embodiments, detection occurs sporadically. In some cases, detection occurs upon a specific event or condition taking place.

As described herein, detection can take place at any suitable position with respect to a microfluidic device. In some cases, one or more detectors is stationery with respect to a microfluidic device during use and/or during detection. For example, a stationery detector may be positioned adjacent a certain region of the microfluidic device, such as a detection region or measurement zone, where one or more events (e.g., a chemical or biological reaction) takes place. The detector may detect, for example, the passing of fluids across the measurement zone. Additionally or alternatively, the detector may detect the binding or association of other components at that region (e.g., the binding of a component to surface of the measurement zone). In some embodiments, a stationery detector may monitor multiple measurement zones simultaneously. For example, a detector such as a camera may be used to image an entire microfluidic device, or large portion of the device, and only certain areas of the device scrutinized. Components such as optical fibers may be used to transmit light from multiple measurement zones to a single detector.

In other embodiments, a detector is removably positioned with respect to the microfluidic device during use and/or during detection. For example, a detector may be physically moved across different regions of the microfluidic device to detect the movement of fluids across the device. For example, a detector may track the movement of certain fluids and/or components in channels of the microfluidic device. Alternatively, the microfluidic device can moved relative to a stationary detector. Other configurations and uses of detectors are also possible.

Figure 2:
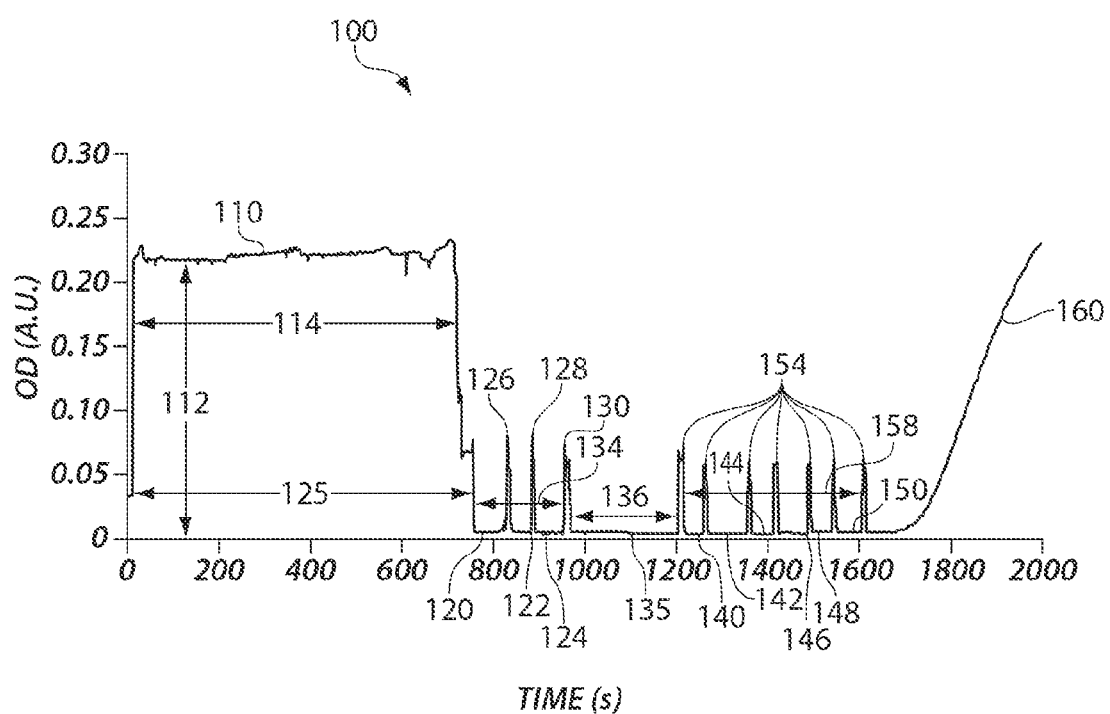
FIG. 2 is a plot showing measurement of optical density as a function of time according to one embodiment.

Examples of signals or patterns of signals that can be used in feedback control are shown in the exemplary embodiment illustrated in FIG. 2. FIG. 2 is a plot showing the detection of various fluids as they flow in a region of a device (e.g., a channel) and pass across a detector. Plot 100 shows the measurement of optical density in arbitrary units (y-axis) as a function of time (x-axis). In certain embodiments, the transmission and/or absorbance of a fluid, for example, can be detected as it passes across a region of a microfluidic system. An optical density of zero may indicate maximum light transmission (e.g., low absorbance) and a higher optical density may indicate low transmission (e.g., higher absorbance). As different fluids flowing across the detector may have different susceptibilities to transmission or absorbance of light, the detection of specific fluids, including their volumes, flow rates, and fluid types, can be determined.

For instance, as shown illustratively in FIG. 2, a first fluid producing signal 110 may pass across the detector at around time=0.1 seconds until approximately 700 seconds. (Time=0 seconds may indicate, for example, the initiation of detection.) First fluid 110 has a particular intensity 112 (e.g., an optical density of about 0.23). If a particular type of fluid having a specific intensity or range of intensities is expected to flow across the detector at a particular point in time (e.g., at a time of approximately 400 seconds after initiation of detection) or between a certain period of time (e.g., sometime between 0 and 800 seconds), the confirmation that this process has occurred can be detected. For example, first fluid producing 110 may, in some embodiments, be a particular type of sample that is to be introduced into the microfluidic device for performing a particular analysis. If the sample type is associated with a particular intensity (e.g., whole blood will give an optical density of approximately 0.23), the type of sample can be verified by determining whether or not that sample has an intensity within an allowed range.

Furthermore, the proper introduction of the sample into the device at a correct time (e.g., at the beginning of the analysis) can be verified by determining where the sample signal occurs as a function of time (along the x-axis). For instance, the time when the sample reaches the measurement zone (observed in an OD having a certain range or intensity) can be monitored. If the sample takes too long to enter the measurement zone, this could indicate, for example, a leak or a clog in the system. If it takes too long for the sample to reach the first measurement zone or there is too much time between the sample or portions of the sample reaching multiple measurement zones (which may be positioned in parallel or in series), the test may be cancelled.

Additionally, the volume of first fluid which produces signal 110 can be determined and verified by measuring time period 114 of the signal. If the particular process to be performed in the microfluidic device requires a sample having a particular volume, this can be verified. For example, a sample having a particular volume (e.g., 10 µL) may be expected, corresponding to an expected range of flow time (e.g., signal having a certain duration) at a certain intensity (e.g., sample OD). The test may ensure that the user correctly loaded the sample into the fluidic connector or other suitable sample introduction device. If the duration of the sample signal is too short (which may indicate not enough sample was introduced) or too long (which may indicate too much sample was introduced) the test may be cancelled and/or the results disregarded.

If, for example, the intensity, time period, or positioning of signal 110 that results from the first fluid is incorrect, the control system may trigger a secondary process that may, for example, modulate fluid flow in the microfluidic system. For example, in one set of embodiments, the control system may determine that since an incorrect sample type or volume was introduce into the device, or introduced into the device at an incorrect time, the analysis to be performed by the microfluidic device should be canceled. In other embodiments, cancelation may occur due to a problem with the device (e.g., a clog in the channels that does not allow fluid to flow at a particular flow rate), or a problem with an analyzer used to analyze the device (e.g., the malfunction of one or more components such as a valve, pump, or vacuum).

The analysis can be canceled, for example, by modulating fluid flow in the microfluidic system (e.g., sending a signal to a pump or a vacuum to stop the flow of fluids), ceasing power to certain components of the system, by ejecting the microfluidic device/cassette from the analyzing system (e.g., automatically or informing a user to do so), or by other processes.

In other embodiments, an abnormality occurring in the system triggers a secondary event to occur, but does not cancel the analysis. In some cases, a user may be alerted that an abnormality has occurred in the system. The user may be informed that results of the test should not be relied upon, that the analysis needs to be performed again, that the analysis may take longer to perform, or that the user should take some action. In some cases, the user can be notified and then asked to verify whether or not one or more processes of the microfluidic system, or the analysis being performed, should be continued. Other methods of quality control are also possible.

In one set of embodiments, a method of conducting quality control to determine abnormalities in operation of a microfluidic system includes detecting a first fluid at (e.g., passing across) a first measurement zone of the microfluidic system and forming a first signal corresponding to the first fluid, and transmitting the first signal to a control system. The first signal may be compared to a reference signal, thereby determining the presence of abnormalities in operation of the microfluidic system. The method may include determining whether to cease operation of the microfluidic system based at least in part on results of the comparing step. In some cases, the control system may determine whether or not to stop an analysis or a portion of an analysis being conducted in the microfluidic system.

As show illustratively in FIG. 2, the type of fluid passing across a detector can be determined at least in part by the intensity of the signal generated by the fluid. For example, whereas signal 110 from a first fluid has a high intensity (e.g., a low light transmission), a second series of fluids producing signals 120, 122 and 124 have a relatively low intensity (e.g., a high light transmission). The plot also indicates the relative separation between the first fluid producing signal 110 and the second fluids producing signals 120, 122 and 124. For instance, the difference between time period 125 and time period 114 can give an indication of how quickly the second set of fluids is flowed across the detector after the first fluid has finished passing across the detector. In some embodiments, this difference in time can be compared with one or more reference signals or values (e.g., a predetermined amount of separation time or time range that is supposed to occur between the first fluid and the second fluids). A difference in time that does not match the reference signal or value, or fall within an allowable range, can indicate that an abnormality has occurred in the microfluidic system. For example, if the time different between time periods 125 and 114 is too long, this may indicate that fluid flow has been obstructed (e.g., due to a clog in a channel by an air bubble or by other means), but later unobstructed in the microfluidic device. In some embodiments, this could influence the test being performed, and as such, the control system may determine whether or not one or more processes should be ceased or modified in the microfluidic system.

As shown illustratively in FIG. 2, second fluids producing signals 120, 122 and 124 are separated by peaks 126, 128 and 130. These peaks represent fluids that are flowed between the second fluids. As described in more detail herein, in some cases these separation fluids may be fluids that are immiscible with the fluids they are separating. For example, in one set of embodiments, second fluids producing signals 120, 122 and 124 are wash solutions that pass across the measurement zone. These wash fluids may be separated by immiscible (separation) fluids (e.g., plugs of air) that produce signals 126, 128 and 130. The wash solutions may have a relatively high transmission, and therefore a relatively low optical density, whereas the plugs of air may have a relatively lower light transmission (e.g., a relatively higher optical density) due to scattering of light as these fluids pass across the detector. Because of the different susceptibility of these fluids to the transmission of light, the different fluids (including the fluid type, phase, volume, flow rate) can be distinguished. In addition, the sequence of second fluids passing across the detector may have a time period 134, which may optionally be compared to an optimal time period or time period range and may optionally be used in feedback control.

In certain embodiments, the number of washes (peaks and troughs) is counted and a control system cancels the analysis if the expected number is not observed. Fewer washes could mean the reagents had evaporated during storage of the device (indicating a leak) or a problem in the connection of the fluidic connector. Too few washes could also indicate that the correct number had not been loaded in the device during device manufacture. Too many washes would indicate that the wash plugs had broken up during storage.

FIG. 2 also shows a third fluid producing signal 135 passing across the measurement zone after the flowing of the second fluids. Since the third fluid has a similar optical density as those of the second set of fluids, the third fluid may be identified or distinguished from other fluids at least in part by its time period 136, which may give an indication of the fluid's volume. The position of time period 136 along the time line (or relative to one or more other signals present) can also give an indication of the fluid being flowed across the measurement zone. For example, the analysis may be designed such that a fluid giving a certain optical density (e.g., ~0.01) and duration (e.g., ~200 seconds at a particular flow rate to be used or pressure to be applied) will occur between 900 seconds and 1200 seconds after the initiation of the analysis. These parameters can be pre-programmed into the control system, and compared with signal 135 measured by the detector.

The third fluid producing signal 135 can be any suitable fluid, and in some cases is reagent to be used in a chemical and/or biological reaction to be performed in the microfluidic device. For example, as described in more detail below, the third fluid may be a detection antibody that may bind with one or more components of the sample. In other embodiments, however, a detection antibody is bound with a component of the sample before the sample flows across the detector. Other configurations of binding a detection antibody are also possible, and in some embodiments, no detection antibody is used at all.

After the third fluid is flowed across the measurement zone, a series of fourth fluids producing signals 140, 142, 144, 146, 148 and 150 may flow across the measurement zone. Each of the fourth fluids may be separated by an immiscible fluid (e.g., air plugs) producing signals 154. In certain embodiments, the frequency of signals having a certain threshold (e.g., air plugs producing signals 154 having a threshold above an optical density of 0.05 and/or a series of fourth fluids having an optical density below 0.01) can be used to trigger one or more events in the microfluidic system.

In some cases, the intensity and frequency of a series of fluids can be combined with a total time period between the first and last of such fluids (e.g., time period 158 encompassing the series of fourth fluids). For example, feedback or the triggering of an event may be based at least in part on the frequency of signals (e.g., peaks) observed in combination with one or more time periods between adjacent signals, and/or in combination with the intensity of the signals, and/or in combination with the time period between the first and last signal of that type or intensity. Optionally, one or more of the signals can be used in combination with the average position of the signals relative to the time scale of events along the time line (e.g., the average time 158 between signals 140 and 150 relative to one or more other signals or reference points (e.g., time=zero)).

In some embodiments, the event that is triggered by a pattern of signals is the modulation of fluid flow within the microfluidic system. For example, one or more of a pump, vacuum, valving system, or other component can be actuated based at least in part on the presence of absence of a particular pattern of signals. As one example, a pattern of signals may trigger the actuation of a valve that allows one or more fluids to flow into a particular channel of the microfluidic device. For instance, actuation of the valve may allow two fluids that are kept separate during storage of the fluids in the device to mix in a common channel In one particular embodiment, a mixed fluid includes an amplification reagent that allows amplification of a signal in a measurement zone of the device. Specific examples are provided in more detail below.

As described herein, a detector may not only detect the passing of fluids across a region of a microfluidic device, but may also detect the presence or absence of an event or condition occurring in a region of the microfluidic device. For example, in some cases a binding event is detected. In other embodiments, the accumulation and/or deposition of a component in a particular region of the microfluidic device is detected. And yet other embodiments, the amplification of a signal is detected. Such processes can occur at any suitable position within a region of a device. For instance, the event or condition may occur within a fluid positioned in the region of the device, on a surface of a channel or chamber of the device, on or in a component positioned within the region of the device (e.g., on a surface of a bead, in a gel, on a membrane).

In some cases, the progression of the event or condition can be determined, and, optionally, compared to one or more reference signals or values (which may be pre-programmed into the control system). For instance, as shown illustratively in FIG. 2, a peak 160 may form due to the build up of a signal (e.g., an opaque layer) in a measurement zone. This slope of the peak may be measured and compared with one or more control values to determine whether or not a correct process is occurring or has occurred in the measurement zone. For example, if the slope of peak 160 is within a particular range of acceptable values, this may indicate that there were no abnormalities in the storage of reagents that were used in part to produce the signal.

In one set of embodiments, peak 160 indicates an amplification reagent entering the measurement zone. The analysis may be designed and configured such that the amplification reagent enters the measurement zone within a certain time period after a certain event takes place (e.g., upon actuation of a valve). In some cases, the amplification reagent should have a certain optical density associated with it (e.g., a low optical density if the reagent is a clear liquid). If the reagent is late in arriving at the measurement zone and/or or the initial optical density is too high, the test can be cancelled. If the reagent has a high optical density (e.g., it is dark or opaque), this could indicate that the reagent has been spoiled (e.g., during storage of the reagent in the device).

In some embodiments, a device may include multiple measurement zones (e.g., in parallel or in series). One measurement zone may be used as a negative control. For instance, minimal binding or deposition of a substance (e.g., an opaque layer), and therefore a low optical density in some embodiments, may be expected in the negative control measurement zone. If a detector measures an elevated optical density in the negative control measurement zone, this may indicate, for example, non-specific binding. In some cases, the signal from this measurement zone can be considered "background" and subtracted from signals in the other measurement zones to account for non-specific binding which may occur throughout the system. If the background is too high, the test may be cancelled. This may, for example, indicate a problem with the amplification reagents or other reagents used in the analysis.

In some embodiments, a device may include a measurement zone used as a positive control. The positive control may, in some embodiments, include a known amount of analyte bound to the measurement zone (e.g., to the channel walls), and the level of the optical density signals at a certain point in time, the slope of these signals, or the change in slope of these signals in the zone may fall within an expected range. These ranges can be determined during calibration of a specified lot of devices. In some cases, as described in more detail herein, this information may be included in the lot-specific information transferred to an analyzer by use of a lot-specific tag, such as a bar-code, memory stick, or radio-frequency identification (RFID) tag. If the reference levels for these measurement zones fall out of range, the test may be cancelled. Similar to background, these signals can also be used to adjust the test signal (e.g., increasing the test signal slightly if these signals are elevated, decreasing the test signal if these signals are low).

The presence of obstructions such as bubbles or other components during one or more events (e.g., amplification, mixing) and/or at one or more unexpected positions in time may indicate problems in the analysis, such as a leak in a valve. These bubbles or other components can be detected as peaks having a certain intensity in the optical density pattern (which may be similar to the air plug peaks used during washing). If these are observed in unexpected places, the test can be cancelled.

It should be understood that while optical density (e.g., transmission or absorbance) was determined in FIG. 2, in other embodiments other types of signals can be measured using a suitable detector. The signals may be produced absent a label (such as in measuring optical density), or produced using a label. A variety of different labels can be used, such as fluorescent markers, dyes, quantum dots, magnetic particles, and other labels known in the art.

As shown illustratively in FIG. 2, in some embodiments an analysis performed in a device can be recorded to produce essentially a "fingerprint" of the analysis. All or potions of the fingerprint may be used to provide feedback to the microfluidic system. In some cases, the fingerprint includes signals from the passing of substantially all fluids used in an analysis across a region of the device. Since different fluids used in the analysis may have different volumes, flow rates, compositions, and other characteristics, these properties can be reflected in the fingerprint. As such, the fingerprint can be used to identify, for example, the fluids used in the analysis, the timing of the fluids (e.g., when particular fluids were introduced into certain regions of the device), interaction of the fluids (e.g., mixing). In some embodiments, the fingerprint can be used to identify the type of analysis performed in the device and/or the test format (e.g., a sandwich assay versus a competitive assay) of the analysis.

In one set of embodiments, the fingerprint as a whole (e.g., the general shape, duration, and timing of all signals) is used to conduct quality control at the end of the analysis. For instance, the fingerprint may be compared with a control fingerprint to determine whether the analysis was run properly after all fluids have been flowed. The control system may, in some cases, notify the user as to whether the analysis was run properly (e.g., via a user interface).

In other embodiments, a detector may be positioned within certain regions of a microfluidic system and may only determine the presence or passing of certain, but not all, fluids across the detector. For example, a detector may be positioned at a mixing region to determine proper mixing of fluids. If the fluids are mixed properly (e.g., a mixed fluid having a certain property such as a certain concentration or volume is produced) or mixed at a proper point in time relative to one or more other events occurring in the analysis, feedback control may allow the mixed fluid to flow into another region of the device. If the mixed fluid does not have one or more desired or predetermined characteristics, feedback control may prevent the mixed fluid may flowing into the region and, in some embodiments, may initiate a second set of fluids to be mixed and transported to the region.

In certain embodiments, feedback control comprises the use of two or more detectors. A first detector may determine a first set of signals, and a second detector may determine a second set of signals. The first and second set of signals may be compared with one another, and/or each may be compared with a set of reference signals or values which may be pre-programmed into a control system. For example, a device may include a plurality of measurement zones, each measurement zone associated with a detector that measures signals in that region. In some cases, the system is designed and configured such that a first detector determines a fingerprint of the analysis that substantially matches the fingerprint of the analysis of a second detector. If the fingerprints do not match, however, this may indicate that an abnormality has occurred within the system. In some cases, the first and/or second detectors may detect the passing of all fluids used in the analysis across a region of the device, or only certain (but not all) fluids passing across a region of the device, as described above. In other embodiments, feedback control, or determination of a value in general, may involve the use of signals detected from multiple measurement zones. For example, flow rate may be determined by measuring how long it takes a bubble or a leading edge of a fluid to travel between two measurement zones.

Feedback control and other processes and methods described herein may be conducted using any suitable microfluidic system, such as those described in more detail below. In some cases, the microfluidic system includes a device or cassette that may be configured to be inserted in a microfluidic sample analyzer. FIGS. 3-6 illustrate various exemplary embodiments of the cassette 20 for use with an analyzer. As shown illustratively in these figures, the cassette 20 may be substantially card-shaped (i.e. similar to a card key) having a substantially rigid plate-like structure. Non-limiting examples of microfluidic systems that can be part of cassette and that can be used with the systems and methods described herein are described in more detail in International Patent Publication No. WO2005/066613 (International Patent Application Serial No. PCT/US2004/043585), filed Dec. 20, 2004 and entitled "Assay Device and Method" and U.S. patent application Ser. No. 12/113,503, published as U.S. Patent Publication No. 2008/0273918, filed May 1, 2008 and entitled "Fluidic Connectors and Microfluidic Systems", each of which are incorporated herein by reference in their entireties for all purposes.

Figure 3:
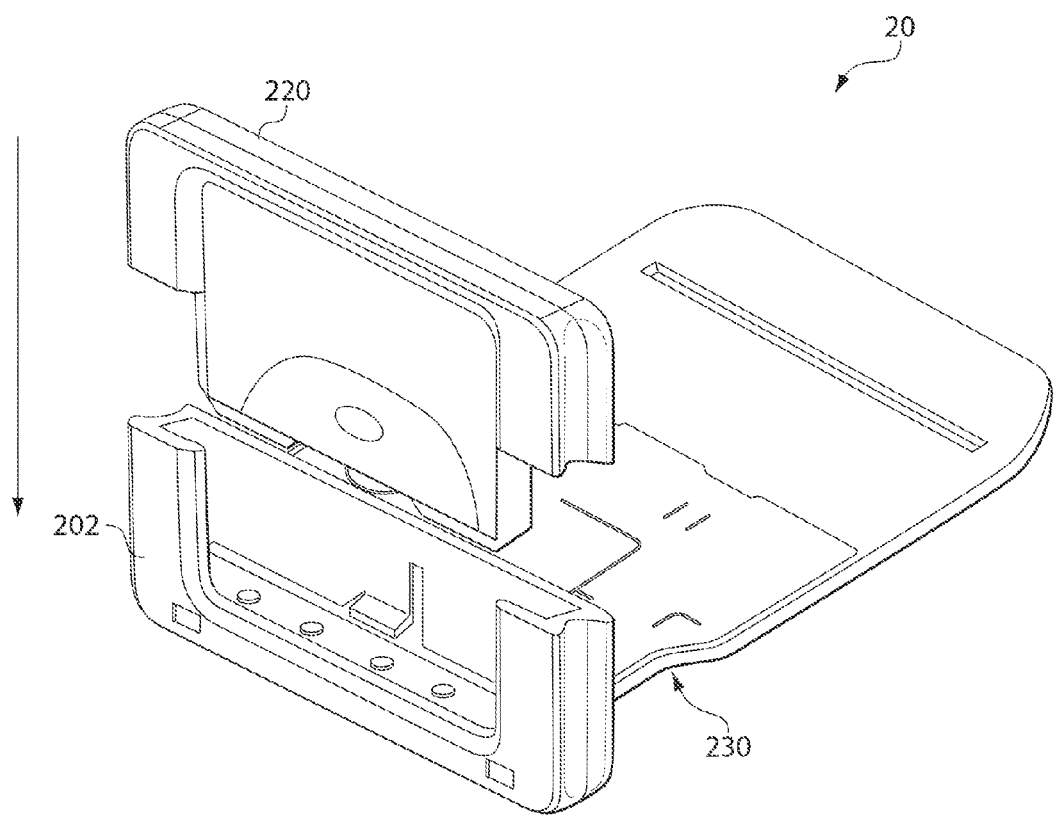
FIG. 3 is a perspective view of a cassette including a fluidic connector according to one embodiment.

The cassette 20 may be configured to include a fluidic connector 220, which as shown in exemplary embodiment illustrated in FIG. 3, may snap into one end of the cassette 20. In certain embodiments, the fluidic connector can be used to introduce one or more fluids (e.g., a sample or a reagent) into the cassette.

In one set of embodiments, the fluidic connector is used to fluidly connect two (or more) channels of the cassette during first use, which channels are not connected prior to first use. For example, the cassette may include two channels that are not in fluid communication prior to first use of the cassette. Non-connected channels may be advantageous in certain cases, such as for storing different reagents in each of the channels. For example, a first channel may be used to store dry reagents and a second channel may be used to store wet reagents. Having the channels be physically separated from one another can enhance long-term stability of the reagents stored in each of the channels, e.g., by keeping the reagent(s) stored in dry form protected from moisture that may be produced by reagent(s) stored in wet form. At first use, the channels may be connected via the fluidic connector to allow fluid communication between the channels of the cassette. For instance, the fluidic connected may puncture seals covering inlets and/or outlets of the cassette to allow insertion of the fluidic connector into the cassette.

As used herein, "prior to first use of the cassette" means a time or times before the cassette is first used by an intended user after commercial sale. First use may include any step(s) requiring manipulation of the device by a user. For example, first use may involve one or more steps such as puncturing a sealed inlet to introduce a reagent into the cassette, connecting two or more channels to cause fluid communication between the channels, preparation of the device (e.g., loading of reagents into the device) before analysis of a sample, loading of a sample onto the device, preparation of a sample in a region of the device, performing a reaction with a sample, detection of a sample, etc. First use, in this context, does not include manufacture or other preparatory or quality control steps taken by the manufacturer of the cassette. Those of ordinary skill in the art are well aware of the meaning of first use in this context, and will be able easily to determine whether a cassette of the invention has or has not experienced first use. In one set of embodiments, cassette of the invention are disposable after first use (e.g., after completion of an assay), and it is particularly evident when such devices are first used, because it is typically impractical to use the devices at all (e.g., for performing a second assay) after first use.

A cassette may be coupled to a fluidic connector using a variety of mechanisms. For example, the fluidic connector may include at least one non-fluidic feature complementary to a feature of the cassette so as to form a non-fluidic connection between the fluidic connector and the cassette upon attachment. The non-fluidic complementary feature may be, for example, a protruding feature of the fluidic connector and corresponding complementary cavities of the cassette, which can help the user align the fluidic connector with the cassette. In some cases, the feature creates a substantial resistance to movement of the fluidic connector relative to the cassette and/or alignment element upon the alignment element receiving the fluidic component (e.g., upon insertion of the fluidic component into the alignment element) and/or during intended use of the device. The fluidic connector and/or cassette may optionally include one or more features such as snap features (e.g., indentations), grooves, openings for inserting clips, zip-tie mechanisms, pressure-fittings, friction-fittings, threaded connectors such as screw fittings, snap fittings, adhesive fittings, magnetic connectors, or other suitable coupling mechanisms. These and other examples of coupling mechanisms are described in more detail in U.S. patent application Ser. No. 12/113,503, published as U.S. Patent Publication No. 2008/0273918, filed May 1, 2008 and entitled "Fluidic Connectors and Microfluidic Systems", which is incorporated herein by reference in its entirety for all purposes. Connection of the fluidic connector to the cassette may involve forming a liquid-tight and/or air-tight seal between the components. Attachment of a fluidic connector to a cassette may be reversible or irreversible.

As shown, the cassette 20 may be configured to include a fluidic connector 220. In particular, the cassette 20 may include a fluidic connector alignment element 202 which is configured to receive and mate with the connector 220. The alignment element may be constructed and arranged to engage with the fluidic connector and thereby position the connector in a predetermined, set configuration relative to the cassette. As shown in the illustrative embodiments of FIG. 3, the cassette may include an alignment element that extends approximately perpendicular to the cassette. In other embodiments, the alignment element may extend approximately parallel to the cassette. Examples of alignment elements are described in more detail in U.S. patent application Ser. No. 12/113,503, published as U.S. Patent Publication No. 2008/0273918, filed May 1, 2008 and entitled "Fluidic Connectors and Microfluidic Systems", which is incorporated herein by reference in its entirety for all purposes.

In some embodiments, the configuration of the alignment element and the fluidic connector may be adapted to allow insertion of the fluidic connector into the alignment element by a sliding motion. For example, the fluidic connector may slide against one or more surfaces of the alignment element when the fluidic connector is inserted into the alignment element.

The fluidic connector may include a substantially U-shaped channel which may hold a fluid and/or reagent (e.g., a fluid sample) prior to be connected to the cassette. The channel may be housed between two shell components which form the connector. In some embodiments, the fluidic connector may be used to collect a sample from the patient prior to the fluidic connector being connected to the cassette. For example, with a blood sample, the fluidic connector may be configured to puncture a patient's finger to collect the sample in the channel In other embodiments, fluid connector does not contain a sample (or reagent) prior to connection to the cassette, but simply allows fluid communication between two or more channels of the cassette upon connection. In one embodiment, the U-shaped channel is formed with a capillary tube. The fluidic connector can also include other channel configurations, and in some embodiments, may include more than one channels that may be fluidically connected or unconnected to one another.

Figure 4:
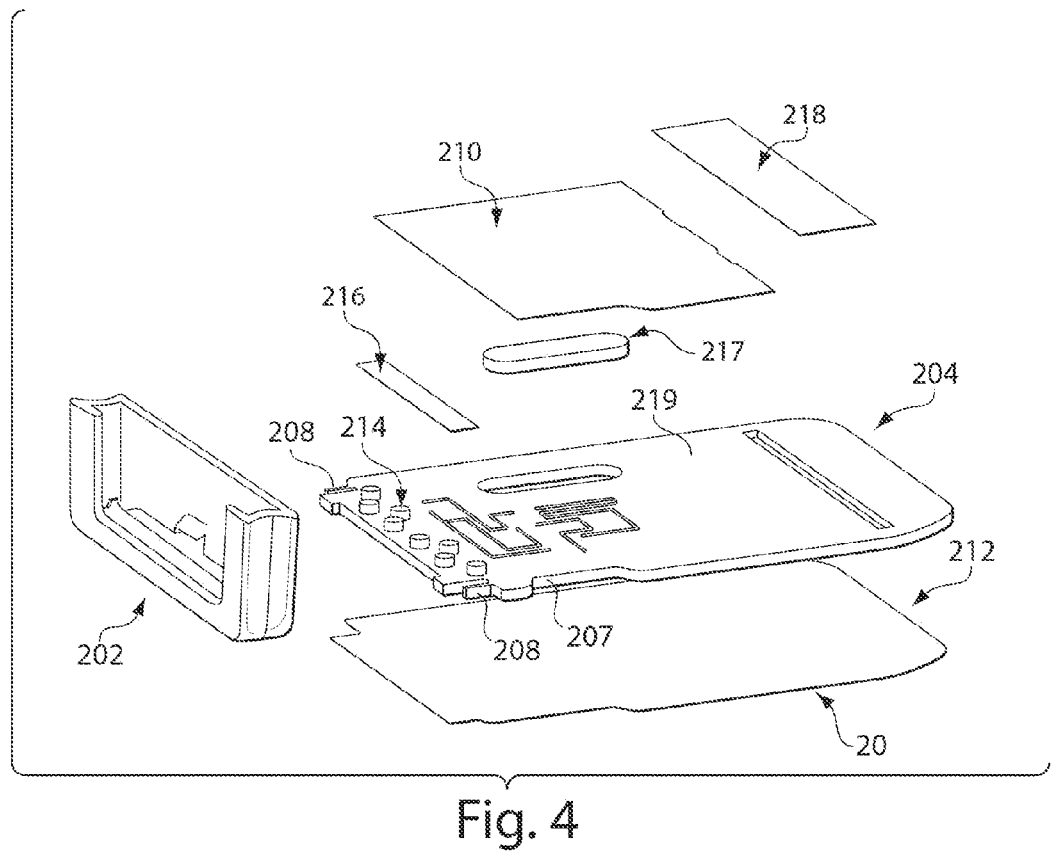
FIG. 4 is a an exploded assembly view of a cassette according to one embodiment.

As shown illustratively in the exploded assembly view of FIG. 4, the cassette 20 may include a cassette body 204 which includes at least one channel 206 configured to receive a sample or reagent. The cassette body 204 may also include latches 208 positioned on one end that interlock with the fluidic connector alignment element 202 for a snap fit.

The cassette 20 may also include top and bottom covers 210 and 212, which may, for example, be made of a transparent material. In some embodiments, a cover can be in the form of a biocompatible adhesive and can be made of a polymer (e.g., PE, COC, PVC) or an inorganic material for example. In some cases, one or more covers are in the form of an adhesive film (e.g., a tape). For some applications, the material and dimensions of a cover are chosen such that the cover is substantially impermeable to water vapor. In other embodiments, the cover can be non-adhesive, but may bond thermally to the microfluidic substrate by direct application of heat, laser energy, or ultrasonic energy. Any inlet(s) and/or outlet(s) of a channel of the cassette can be sealed (e.g., by placing an adhesive over the inlet(s) and/or outlet(s)) using one or more covers. In some cases, the cover substantially seals one or more stored reagents in the cassette.

As illustrated, the cassette body 204 may include one or more ports 214 coupled to the channel 206 in the cassette body 204. These ports 214 can be configured to align with the substantially U-shaped channel 222 in the fluidic connector 220 when the fluidic connector 220 is coupled to the cassette 20 to fluidly connect the channel 206 in the cassette body 204 with the channel 222 in the fluidic connector 220. As shown, a cover 216 may be provided over the ports 214 and the cover 216 may be configured to be pieced or otherwise opened (e.g., by the connector 220 or by other means) to fluidly connect the two channels 206 and 222. Additionally, a cover 218 may be provided to cover port 219 (e.g., a vacuum port) in the cassette body 204. As set forth in further detail below, the port 219 may be configured to fluidly connect a fluid flow source 40 with the channel 206 to move a sample through the cassette. The cover 218 over the port 219 may be configured to be pierced or otherwise opened to fluidly connect the channel 206 with the fluid flow source 40.

The cassette body 204 may optionally include a liquid containment region such as a waste area, including an absorbent material 217 (e.g., a waste pad). In some embodiments, the liquid containment region includes regions that capture one or more liquids flowing in the cassette, while allowing gases or other fluids in the cassette to pass through the region. This may be achieved, in some embodiments, by positioning one or more absorbent materials in the liquid containment region for absorbing the liquids. This configuration may be useful for removing air bubbles from a stream of fluid and/or for separating hydrophobic liquids from hydrophilic liquids. In certain embodiments, the liquid containment region prevents liquids from passing through the region. In some such cases, the liquid containment region may act as a waste area by capturing substantially all of the liquid in the cassette, thereby preventing liquids from exiting the cassette (e.g., while allowing gases to escape from an outlet of the cassette). For example, the waste area may be used to store the sample and/or reagents in the cassette after they have passed through the channel 206 during the analysis of the sample. These and other arrangements may be useful when the cassette is used as a diagnostic tool, as the liquid containment region may prevent a user from being exposed to potentially-harmful fluids in the cassette. Non-limiting examples of liquid containment regions are described in more detail in U.S. patent application Ser. No. 12/196,392, published as U.S. Patent Publication No. 2009/0075390, filed Aug. 22, 2008, entitled "Liquid containment for integrated assays", which is incorporated herein by reference in its entirety for all purposes.

Figure 5:
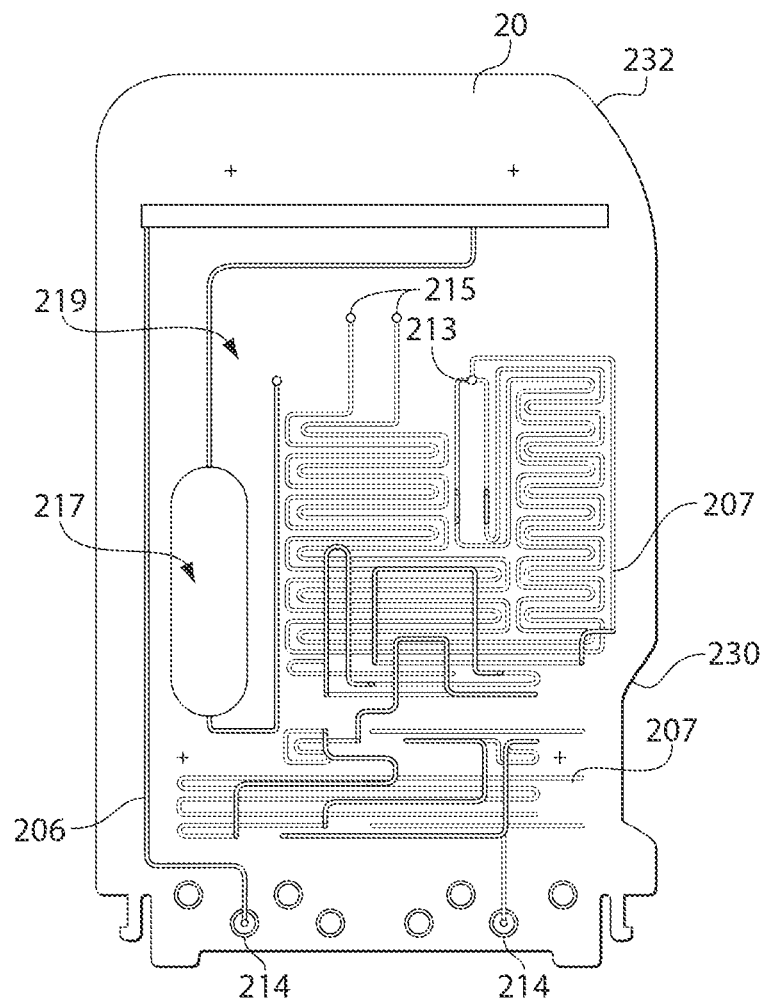
FIG. 5 is a schematic view of a cassette according to one embodiment.
Figure 6:
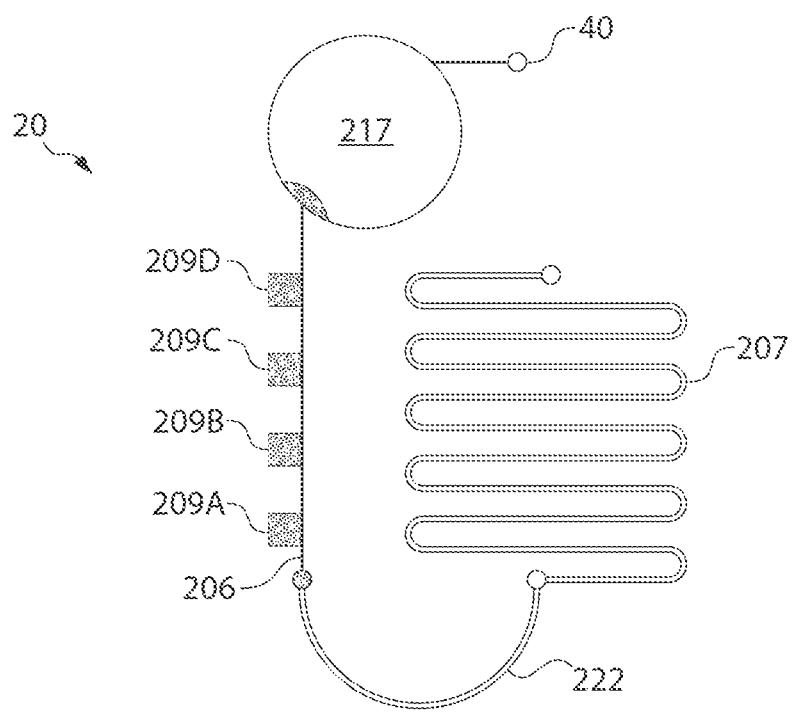
FIG. 6 is a diagram showing a microfluidic system of a cassette including a fluidic connector according to one embodiment.

FIG. 5 shows a cassette having a certain configuration of channels and including various components of a microfluidic system for manipulating fluids. FIG. 6 shows another example of a configuration of channels that may be part of a cassette. As shown illustratively in FIGS. 5 and 6, in some embodiments, a cassette may include a first channel 206 and a second channel 207 spaced apart from the first channel In one embodiment, the channels 206, 207 range in largest cross-section dimension from approximately 50 micrometers to approximately 500 micrometers, although other channel sizes and configurations may be used, as described in more detail below.

The first channel 206 may include one or more measurement zones used to analyze the sample. For example, in one illustrative embodiment, the channel 206 includes four measurement zones 209 which are utilized during sample analysis (see FIG. 6).

In certain embodiments, one or more measurement zones are the form of meandering regions (e.g., involving meandering channels), as described in more detail below and in International Patent Publication No. WO2006/113727 (International Patent Application Serial No. PCT/US06/14583), filed Apr. 19, 2006 and entitled "Fluidic Structures Including Meandering and Wide Channels"; U.S. patent application Ser. No. 12/113,503, published as U.S. Patent Publication No. 2008/0273918, filed May 1, 2008 and entitled "Fluidic Connectors and Microfluidic Systems" and U.S. patent application Ser. No. 12/196,392, published as U.S. Patent Publication No. 2009/0075390, filed Aug. 22, 2008, entitled "Liquid containment for integrated assays", each of which is incorporated herein by reference in their entireties for all purposes. A meandering region may, for example, be defined by an area of at least 0.25 mm$^2$, at least 0.5 mm$^2$, at least 0.75 mm$^2$, or at least 1.0 mm$^2$, wherein at least 25%, 50%, or 75% of the area of the meandering region comprises an optical detection pathway. A detector that allows measurement of a single signal through more than one adjacent segments of the meandering region may be positioned adjacent the meandering region.

As described herein, the first channel 206 and/or the second channel 207 may be used to store one or more reagents used to process and analyze the sample prior to first use of the cassette. In some embodiments, dry reagents are stored in one channel or section of a cassette and wet reagents are stored in a second channel or section of cassette. Alternatively, two separate sections or channels of a cassette may both contain dry reagents and/or wet reagents. Reagents can be stored and/or disposed, for example, as a liquid, a gas, a gel, a plurality of particles, or a film. The reagents may be positioned in any suitable portion of a cassette, including, but not limited to, in a channel, reservoir, on a surface, and in or on a membrane, which may optionally be part of a reagent storage area. A reagent may be associated with a cassette (or components of a cassette) in any suitable manner. For example, reagents may be crosslinked (e.g., covalently or ionically), absorbed, or adsorbed (physisorbed) onto a surface within the cassette. In one particular embodiment, all or a portion of a channel (such as a fluid path of a fluid connector or a channel of the cassette) is coated with an anti-coagulant (e.g., heparin). In some cases, a liquid is contained within a channel or reservoir of a cassette prior to first use and/or prior to introduction of a sample into the cassette.

In some embodiments, the stored reagents may include fluid plugs positioned in linear order so that during use, as fluids flow to a reaction site, they are delivered in a predetermined sequence. A cassette designed to perform an assay, for example, may include, in series, a rinse fluid, a labeled-antibody fluid, a rinse fluid, and a amplification fluid, all stored therein. While the fluids are stored, they may be kept separated by substantially immiscible separation fluids (e.g., a gas such as air) so that fluid reagents that would normally react with each other when in contact may be stored in a common channel.

Reagents can be stored in a cassette for various amounts of time. For example, a reagent may be stored for longer than 1 hour, longer than 6 hours, longer than 12 hours, longer than 1 day, longer than 1 week, longer than 1 month, longer than 3 months, longer than 6 months, longer than 1 year, or longer than 2 years. Optionally, the cassette may be treated in a suitable manner in order to prolong storage. For instance, cassettes having stored reagents contained therein may be vacuum sealed, stored in a dark environment, and/or stored at low temperatures (e.g., below 0 degrees C.). The length of storage depends on one or more factors such as the particular reagents used, the form of the stored reagents (e.g., wet or dry), the dimensions and materials used to form the substrate and cover layer(s), the method of adhering the substrate and cover layer(s), and how the cassette is treated or stored as a whole.

As illustrated in the exemplary embodiment shown in FIGS. 5 and 6, channels 206 and 207 may not be in fluid communication with each other until the fluidic connector 220 is coupled to the cassette 20. In other words, the two channels, in some embodiments, are not in fluid communication with one another prior to first use and/or prior to introduction of a sample into the cassette. In particular, as illustrated, the substantially U-shaped channel 222 of the connector 220 may fluidly connect the first and second channels 206, 207 such that the reagents in the second channel 207 can pass through the U-shaped channel 22 and selectively move into the measurement zones 209 in the first channel 206. In other embodiments, the two channels 206 and 207 are in fluid communication with one another prior to first use, and/or prior to introduction of a sample into the cassette, but the fluidic connector further connects the two channels (e.g., to form a closed-loop system) upon first use.

In some embodiments, a cassette described herein may include one more microfluidic channels, although such cassettes are not limited to microfluidic systems and may relate to other types of fluidic systems. "Microfluidic," as used herein, refers to a cassette, device, apparatus or system including at least one fluid channel having a maximum cross-sectional dimension of less than 1 mm, and a ratio of length to largest cross-sectional dimension of at least 3:1. A "microfluidic channel," as used herein, is a channel meeting these criteria.

The "cross-sectional dimension" (e.g., a diameter) of the channel is measured perpendicular to the direction of fluid flow. Most fluid channels in components of cassettes described herein have maximum cross-sectional dimensions less than 2 mm, and in some cases, less than 1 mm In one set of embodiments, all fluid channels of a cassette are microfluidic or have a largest cross sectional dimension of no more than 2 mm or 1 mm In another set of embodiments, the maximum cross-sectional dimension of the channel(s) are less than 500 microns, less than 200 microns, less than 100 microns, less than 50 microns, or less than 25 microns. In some cases the dimensions of the channel may be chosen such that fluid is able to freely flow through the article or substrate. The dimensions of the channel may also be chosen, for example, to allow a certain volumetric or linear flowrate of fluid in the channel. Of course, the number of channels and the shape of the channels can be varied by any suitable method known to those of ordinary skill in the art. In some cases, more than one channel or capillary may be used.

A channel may include a feature on or in an article (e.g., a cassette) that at least partially directs the flow of a fluid. The channel can have any suitable cross-sectional shape (circular, oval, triangular, irregular, square or rectangular, or the like) and can be covered or uncovered. In embodiments where it is completely covered, at least one portion of the channel can have a cross-section that is completely enclosed, or the entire channel may be completely enclosed along its entire length with the exception of its inlet(s) and outlet(s). A channel may also have an aspect ratio (length to average cross sectional dimension) of at least 2:1, more typically at least 3:1, 5:1, or 10:1 or more.

Cassettes described herein may include channels or channel segments positioned on one or two sides of the cassette. In some cases, the channels are formed in a surface of the cassette. The channel segments may be connected by an intervening channel passing through the cassette. Non-limiting examples of such and other channel configurations are described in more detail in U.S. patent application Ser. No. 12/640,420, filed Dec. 17, 2009, entitled, "Reagent Storage in Microfluidic Systems and Related Articles and Methods", which is incorporated herein by reference in its entirety for all purposes. In some embodiments, the channel segments are used to store reagents in the device prior to first use by an end user. The specific geometry of the channel segments and the positions of the channel segments within the cassettes may allow fluid reagents to be stored for extended periods of time without mixing, even during routine handling of the cassettes such as during shipping of the cassettes, and when the cassettes are subjected to physical shock or vibration.

In certain embodiments, a cassette includes optical elements that are fabricated on one side of a cassette opposite a series of fluidic channels. An "optical element" is used to refer to a feature formed or positioned on or in an article or cassette that is provided for and used to change the direction (e.g., via refraction or reflection), focus, polarization, and/or other property of incident electromagnetic radiation relative to the light incident upon the article or cassette in the absence of the element. For example, an optical element may comprise a lens (e.g., concave or convex), mirror, grating, groove, or other feature formed or positioned in or on a cassette. A cassette itself absent a unique feature, however, would not constitute an optical element, even though one or more properties of incident light may change upon interaction with the cassette. The optical elements may guide incident light passing through the cassette such that most of the light is dispersed away from specific areas of the cassette, such as intervening portions between the fluidic channels. By decreasing the amount of light incident upon these intervening portions, the amount of noise in a detection signal can be decreased when using certain optical detection systems. In some embodiments, the optical elements comprise triangular grooves formed on or in a surface of the cassette. The draft angle of the triangular grooves may be chosen such that incident light normal to the surface of the cassette is redirected at an angle dependent upon the indices of refraction of the external medium (e.g., air) and the cassette material. In some embodiments, one or more optical elements are positioned between adjacent segments of a meandering region of a measurement zone. Non-limiting examples of optical elements and configurations of channels and components with respect to the optical elements are described in more detail in U.S. patent application Ser. No. 12/698,451, filed Feb. 2, 2010, entitled, "Structures for Controlling Light Interaction with Microfluidic Devices", which is incorporated herein by reference in its entirety for all purposes.

A cassette can be fabricated of any material suitable for forming a channel Non-limiting examples of materials include polymers (e.g., polyethylene, polystyrene, polymethylmethacrylate, polycarbonate, poly(dimethylsiloxane), PTFE, PET, and a cyclo-olefin copolymer), glass, quartz, and silicon. The material forming the cassette and any associated components (e.g., a cover) may be hard or flexible. Those of ordinary skill in the art can readily select suitable material(s) based upon e.g., its rigidity, its inertness to (e.g., freedom from degradation by) a fluid to be passed through it, its robustness at a temperature at which a particular device is to be used, its transparency/opacity to light (e.g., in the ultraviolet and visible regions), and/or the method used to fabricate features in the material. For instance, for injection molded or other extruded articles, the material used may include a thermoplastic (e.g., polypropylene, polycarbonate, acrylonitrile-butadiene-styrene, nylon 6), an elastomer (e.g., polyisoprene, isobutene-isoprene, nitrile, neoprene, ethylene-propylene, hypalon, silicone), a thermoset (e.g., epoxy, unsaturated polyesters, phenolics), or combinations thereof.

In some embodiments, the material and dimensions (e.g., thickness) of a cassette and/or cover are chosen such that it is substantially impermeable to water vapor. For instance, a cassette designed to store one or more fluids therein prior to first use may include a cover comprising a material known to provide a high vapor barrier, such as metal foil, certain polymers, certain ceramics and combinations thereof. In other cases, the material is chosen based at least in part on the shape and/or configuration of the cassette. For instance, certain materials can be used to form planar devices whereas other materials are more suitable for forming devices that are curved or irregularly shaped.

In some instances, a cassette is comprised of a combination of two or more materials, such as the ones listed above. For instance, channels of the cassette may be formed in polystyrene or other polymers (e.g., by injection molding) and a biocompatible tape may be used to seal the channels. The biocompatible tape or flexible material may include a material known to improve vapor barrier properties (e.g., metal foil, polymers or other materials known to have high vapor barriers), and may optionally allow access to inlets and outlets by puncturing or unpeeling the tape. A variety of methods can be used to seal a microfluidic channel or portions of a channel, or to join multiple layers of a device, including but not limited to, the use of adhesives, use adhesive tapes, gluing, bonding, lamination of materials, or by mechanical methods (e.g., clamping, snapping mechanisms, etc.).

In some instances, a cassette comprises a combination of two or more separate layers (or cassettes) mounted together. Independent channel networks (such as sections 71 and 77 of FIG. 1A), which may optionally include reagents stored therein prior to first use, may be included on separate layers (or cassettes). The separate layers may be mounted together by any suitable means, such as by the methods described herein, to form a single cassette. In some embodiments, two or more channel networks are connected fluidically at first use, e.g., by use of a fluidic connector. In other embodiments, two or more channel networks are connected fluidically prior to first use.

A cassette described herein may have any suitable volume for carrying out an analysis such as a chemical and/or biological reaction or other process. The entire volume of a cassette includes, for example, any reagent storage areas, measurement zones, liquid containment regions, waste areas, as well as any fluid connectors, and fluidic channels associated therewith. In some embodiments, small amounts of reagents and samples are used and the entire volume of the fluidic device is, for example, less than 10 mL, 5 mL, 1 mL, 500 µL, 250 µL, 100 µL, 50 µL, 25 µL, 10 µL, 5 pL, or 1 µL.

A cassette described herein may be portable and, in some embodiments, handheld. The length and/or width of the cassette may be, for example, less than or equal to 20 cm, 15 cm, 10 cm, 8 cm, 6 cm, or 5 cm. The thickness of the cassette may be, for example, less than or equal to 5 cm, 3 cm, 2 cm, 1 cm, 8 mm, 5 mm, 3 mm, 2 mm, or 1 mm Advantageously, portable devices may be suitable for use in point-of-care settings.

It should be understood that the cassettes and their respective components described herein are exemplary and that other configurations and/or types of cassettes and components can be used with the systems and methods described herein.

The methods and systems described herein may involve variety of different types of analyses, and can be used to determine a variety of different samples. In some cases, an analysis involves a chemical and/or biological reaction. In some embodiments, a chemical and/or biological reaction involves binding. Different types of binding may take place in cassettes described herein. Binding may involve the interaction between a corresponding pair of molecules that exhibit mutual affinity or binding capacity, typically specific or non-specific binding or interaction, including biochemical, physiological, and/or pharmaceutical interactions. Biological binding defines a type of interaction that occurs between pairs of molecules including proteins, nucleic acids, glycoproteins, carbohydrates, hormones and the like. Specific examples include antibody/antigen, antibody/hapten, enzyme/substrate, enzyme/inhibitor, enzyme/cofactor, binding protein/substrate, carrier protein/substrate, lectin/carbohydrate, receptor/hormone, receptor/effector, complementary strands of nucleic acid, protein/nucleic acid repressor/inducer, ligand/cell surface receptor, virus/ligand, etc. Binding may also occur between proteins or other components and cells. In addition, devices described herein may be used for other fluid analyses (which may or may not involve binding and/or reactions) such as detection of components, concentration, etc.

In some cases, a heterogeneous reaction (or assay) may take place in a cassette; for example, a binding partner may be associated with a surface of a channel, and the complementary binding partner may be present in the fluid phase. Other solid-phase assays that involve affinity reaction between proteins or other biomolecules (e.g., DNA, RNA, carbohydrates), or non-naturally occurring molecules, can also be performed. Non-limiting examples of typical reactions that can be performed in a cassette include chemical reactions, enzymatic reactions, immuno-based reactions (e.g., antigen-antibody), and cell-based reactions.

Non-limiting examples of analytes that can be determined (e.g., detected) using cassettes described herein include specific proteins, viruses, hormones, drugs, nucleic acids and polysaccharides; specifically antibodies, e.g., IgD, IgG, IgM or IgA immunoglobulins to HTLV-I, HIV, Hepatitis A, B and non A/non B, Rubella, Measles, Human Parvovirus B19, Mumps, Malaria, Chicken Pox or Leukemia; human and animal hormones, e.g., thyroid stimulating hormone (TSH), thyroxine (T4), luteinizing hormone (LH), follicle-stimulating hormones (FSH), testosterone, progesterone, human chorionic gonadotropin, estradiol; other proteins or peptides, e.g. troponin I, c-reactive protein, myoglobin, brain natriuretic protein, prostate specific antigen (PSA), free-PSA, complexed-PSA, pro-PSA, EPCA-2, PCADM-1, ABCAS, hK2, beta-MSP (PSP94), AZGP1, Annexin A3, PSCA, PSMA, JM27, PAP; drugs, e.g., paracetamol or theophylline; marker nucleic acids, e.g., PCA3, TMPRS-ERG; polysaccharides such as cell surface antigens for HLA tissue typing and bacterial cell wall material. Chemicals that may be detected include explosives such as TNT, nerve agents, and environmentally hazardous compounds such as polychlorinated biphenyls (PCBs), dioxins, hydrocarbons and MTBE. Typical sample fluids include physiological fluids such as human or animal whole blood, blood serum, blood plasma, semen, tears, urine, sweat, saliva, cerebro-spinal fluid, vaginal secretions; in-vitro fluids used in research or environmental fluids such as aqueous liquids suspected of being contaminated by the analyte.

In some embodiments, one or more reagents that can be used to determine an analyte of a sample (e.g., a binding partner of the analyte to be determined) is stored in a channel or chamber of a cassette prior to first use in order to perform a specific test or assay. In cases where an antigen is being analyzed, a corresponding antibody or aptamer can be the binding partner associated with a surface of a microfluidic channel If an antibody is the analyte, then an appropriate antigen or aptamer may be the binding partner associated with the surface. When a disease condition is being determined, it may be preferred to put the antigen on the surface and to test for an antibody that has been produced in the subject. Such antibodies may include, for example, antibodies to HIV.

In some embodiments, a cassette is adapted and arranged to perform an analysis involving accumulating an opaque material on a region of a microfluidic channel, exposing the region to light, and determining the transmission of light through the opaque material. An opaque material may include a substance that interferes with the transmittance of light at one or more wavelengths. An opaque material does not merely refract light, but reduces the amount of transmission through the material by, for example, absorbing or reflecting light. Different opaque materials or different amounts of an opaque material may allow transmittance of less than, for example, 90, 80, 70, 60, 50, 40, 30, 20, 10 or 1 percent of the light illuminating the opaque material. Examples of opaque materials include molecular layers of metal (e.g., elemental metal), ceramic layers, polymeric layers, and layers of an opaque substance (e.g., a dye). The opaque material may, in some cases, be a metal that can be electrolessly deposited. These metals may include, for example, silver, copper, nickel, cobalt, palladium, and platinum.

An opaque material that forms in a channel may include a series of discontinuous independent particles that together form an opaque layer, but in one embodiment, is a continuous material that takes on a generally planar shape. The opaque material may have a dimension (e.g., a width of length) of, for example, greater than or equal to 1 micron, greater than or equal to 5 microns, greater than 10 microns, greater than or equal to 25 microns, or greater than or equal to 50 microns. In some cases, the opaque material extends across the width of the channel (e.g., a measurement zone) containing the opaque material. The opaque layer may have a thickness of, for example, less than or equal to 10 microns, less than or equal to 5 microns, less than or equal to 1 micron, less than or equal to 100 nanometers or less than or equal to 10 nanometers. Even at these small thicknesses, a detectable change in transmittance can be obtained. The opaque layer may provide an increase in assay sensitivity when compared to techniques that do not form an opaque layer.

In one set of embodiments, a cassette described herein is used for performing an immunoassay (e.g., for human IgG or PSA) and, optionally, uses silver enhancement for signal amplification. A cassette described herein may have one or more similar characteristics as those described in U.S. patent application Ser. No. 12/113,503, published as U.S. Patent Publication No. 2008/0273918, filed May 1, 2008 and entitled "Fluidic Connectors and Microfluidic Systems", which is incorporated herein by reference. In such an immunoassay, after delivery of a sample containing human IgG to a reaction site or analysis region, binding between the human IgG and anti-human IgG can take place. One or more reagents, which may be optionally stored in a channel of the device prior to use, can then flow over this binding pair complex. One of the stored reagents may include a solution of metal colloid (e.g., a gold conjugated antibody) that specifically binds to the antigen to be detected (e.g., human IgG). This metal colloid can provide a catalytic surface for the deposition of an opaque material, such as a layer of metal (e.g., silver), on a surface of the analysis region. The layer of metal can be formed by using a two component system: a metal precursor (e.g., a solution of silver salts) and a reducing agent (e.g., hydroquinone, chlorohydroquinone, pyrogallol, metol, 4-aminophenol and phenidone), which can optionally be stored in different channels prior to use.

As a positive or negative pressure differential is applied to the system, the silver salt and reducing solutions can merge at a channel intersection, where they mix (e.g., due to diffusion) in a channel, and then flow over the analysis region. Therefore, if antibody-antigen binding occurs in the analysis region, the flowing of the metal precursor solution through the region can result in the formation of an opaque layer, such as a silver layer, due to the presence of the catalytic metal colloid associated with the antibody-antigen complex. The opaque layer may include a substance that interferes with the transmittance of light at one or more wavelengths. An opaque layer that is formed in the channel can be detected optically, for example, by measuring a reduction in light transmittance through a portion of the analysis region (e.g., a serpentine channel region) compared to a portion of an area that does not include the antibody or antigen. Alternatively, a signal can be obtained by measuring the variation of light transmittance as a function of time, as the film is being formed in an analysis region. The opaque layer may provide an increase in assay sensitivity when compared to techniques that do not form an opaque layer. Additionally, various amplification chemistries that produce optical signals (e.g., absorbance, fluorescence, glow or flash chemiluminescence, electrochemiluminescence), electrical signals (e.g., resistance or conductivity of metal structures created by an electroless process) or magnetic signals (e.g., magnetic beads) can be used to allow detection of a signal by a detector.

Various types of fluids can be used with the cassettes described herein. As described herein, fluids may be introduced into the cassette at first use, and/or stored within the cassette prior to first use. Fluids include liquids such as solvents, solutions and suspensions. Fluids also include gases and mixtures of gases. When multiple fluids are contained in a cassette, the fluids may be separated by another fluid that is preferably substantially immiscible in each of the first two fluids. For example, if a channel contains two different aqueous solutions, a separation plug of a third fluid may be substantially immiscible in both of the aqueous solutions. When aqueous solutions are to be kept separate, substantially immiscible fluids that can be used as separators may include gases such as air or nitrogen, or hydrophobic fluids that are substantially immiscible with the aqueous fluids. Fluids may also be chosen based at least in part on the fluid's reactivity with adjacent fluids. For example, an inert gas such as nitrogen may be used in some embodiments and may help preserve and/or stabilize any adjacent fluids. An example of an substantially immiscible liquid for separating aqueous solutions is perfluorodecalin. The choice of a separator fluid may be made based on other factors as well, including any effect that the separator fluid may have on the surface tension of the adjacent fluid plugs. It may be preferred to maximize the surface tension to promote retention of the fluid plug as a single continuous unit under varying environmental conditions such as vibration, shock and temperature variations. Separator fluids may also be inert to a reaction site (e.g., measurement zone) to which the fluids will be supplied. For example, if a reaction site includes a biological binding partner, a separator fluid such as air or nitrogen may have little or no effect on the binding partner. The use of a gas (e.g., air) as a separator fluid may also provide room for expansion within a channel of a fluidic device should liquids contained in the device expand or contract due to changes such as temperature (including freezing) or pressure variations.

As described herein, a cassette may be configured to operate with an analyzer in some embodiments. For example, the cassette shown illustratively in FIG. 5 may have a cammed surface along a side portion of the cassette. In this particular embodiment, the cammed surface includes a notch 230 formed at one end of the cassette. The other end of the cassette includes a curved surface 232. This cammed surface of the cassette may be configured to interact with a sample analyzer such that the analyzer can detect the presence of the cassette within the housing of the analyzer and/or position the cassette within the analyzer.

Figure 7:
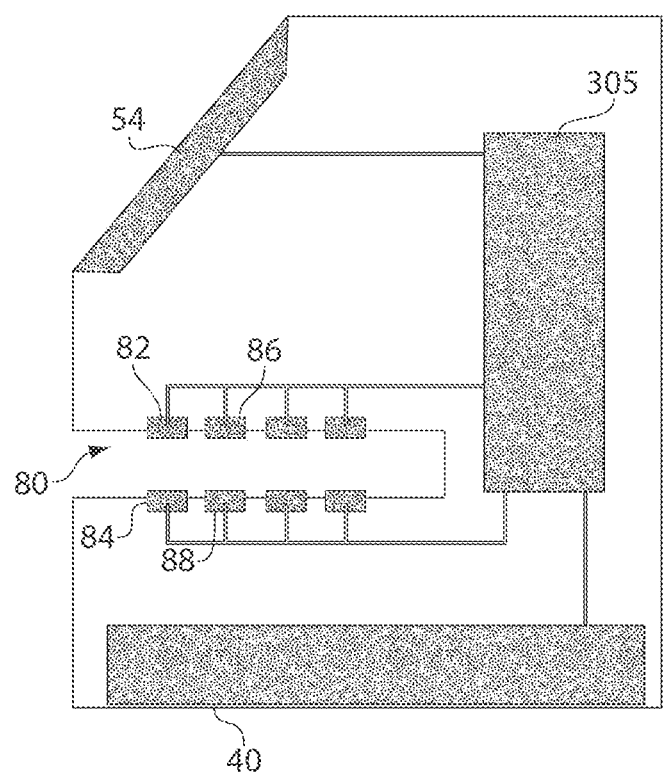
FIG. 7 is a schematic view of a portion of a sample analyzer according to one embodiment.

FIG. 7 shows an example of an analyzer 301 that may be configured to receive a cassette. The analyzer may include a fluid flow source 40 (e.g., a pressure-control system) which may be fluidly connected to the channels 206, 207, 222 (e.g., of FIG. 6) to pressurize the channels to move the sample and/or other reagents through the channels. In particular, the fluid flow source 40 may be configured to move a sample and/or reagent initially from the substantially U-shaped channel 222 into the first channel 206. The fluid flow source 40 may also be used to move the reagents in the second channel 207 through the substantially U-shaped channel 222 and into the first channel 206. After the sample and reagents pass through the measurement zones 209 and are analyzed, the fluid flow source 40 may be configured to move the fluids into the absorbent material 217 of the cassette 200. In one embodiment, the fluid flow source is a vacuum system. It should be understood, however, that other sources of fluid flow such as valves, pumps, and/or other components can be used.

Analyzer 301 may be used in a variety of ways to process and analyze a sample placed within the analyzer. In one particular embodiment, once a mechanical component configured to interface with the cassette indicates that the cassette 20 is properly loaded in the analyzer 301, the identification reader reads and identifies information associated with the cassette 20. The analyzer 301 may be configured to compare the information to data stored in a control system to ensure that it has calibration information for this particular sample (such as a calibration curve or expected values for any measurements made during an assay). In the event that the analyzer does not have the proper calibration information, the analyzer may output a request to the user to upload the specific information needed. This information can be uploaded using, for example, the same identification reader which reads the cassette information. It could also be uploaded using a separate identification reader or by some other method. The analyzer may also be configured to review expiration date information associated with the cassette and cancel the analysis if the expiration date has passed.

In one embodiment, once the analyzer has determined that the cassette may be analyzed, a fluid flow source such as a vacuum manifold may be configured to contact the cassette to ensure a fluid-tight seal around a vacuum port and vent ports of the cassette. In one embodiment, an optical system may take initial measurements to obtain reference readings. Such reference readings may be taken both with light sources (e.g., 82, 86 of FIG. 7) activated and deactivated.

To initiate movement of the sample, fluid flow source 40 (e.g., a vacuum system) may be activated, which may rapidly change the pressure within the channel 206, 207 (e.g., reduced to approximately −30 kPa). This reduction of pressure within the channel may drive the sample into the channel 206 and through each of the measurement zones 209A-209D (see FIG. 6). After the sample reaches the final measurement zone 209D, the sample may continue to flow into the liquid containment region 217.

In one particular embodiment, the microfluidic sample analyzer 301 is used to measure the level of a prostate specific antigen (PSA) in a blood sample. In this embodiment, four measurement zones 209A-209D may be utilized to analyze the sample. For example, in a first measurement zone, the walls of the channel may be blocked with a blocking protein (such as Bovine Serum Albumin) such that little or no proteins in the blood sample attach to the walls of the measurement zone 209 (except for perhaps some non-specific binding which may be washed off). This first measurement zone may act as a negative control.

In a second measurement zone 209, the walls of the channel 206 may be coated with a predetermined large quantity of a prostate specific antigen (PSA) to act as a high or positive control. As the blood sample passes through the second measurement zone 209, little or no PSA proteins in the blood may bind to the walls of the channel. Gold conjugated signal antibodies in the sample may be dissolved from inside of the fluidic connector tube 222 or may be flowed from any other suitable location. These antibodies may not yet be bound to the PSA in the sample, and thus they may bind to the PSA on the walls of the channel to act as a high or positive control.

In a third measurement zone 209, the walls of the channel 206 may be coated with a predetermined small quantity of PSA to act as a low control. As the blood sample flows through this measurement zone 209, no PSA proteins in the sample bind to the wall of the channel. Gold conjugated signal antibodies in the sample may be dissolved from inside of the fluidic connector tube 222 (which are not yet bound to the PSA in the sample) or may be flowed from any other suitable location, and may bind to the PSA on the walls of the channel to act as a low control.

In a fourth measurement zone 209, the walls of the channel 206 may be coated with the capture antibody, an anti-PSA antibody, which binds to a different epitope on the PSA protein than the gold conjugated signal antibody. As the blood sample flows through the fourth measurement zone, PSA proteins in the blood sample may bind to the anti-PSA antibody in a way that is proportional to the concentration of these proteins in the blood. Thus, in one embodiment, the first three measurement zones 209 may act as controls and the fourth measurement zone 209 may actually test the sample.

In some instances, measurements from a region that analyzes the sample (e.g., the fourth measurement zone described above) can be used not only to determine the concentration of an analyte in a sample, but also as a control as well. For example, a threshold measurement can be established at an early phase of amplification. Measurements above this value (or below this value) may indicate that the concentration of analyte is outside the desired range for the assay. This technique may be used to identify, for example, whether a High Dose Hook Effect is taking place during the analysis, i.e., when a very high concentration of analyte gives an artificially low reading.

In other embodiments, different numbers of measurement zones can be provided, and an analysis may optionally include more than one measurement zones that actually test the sample. Additional measurement zones can be used to measure additional analytes so that the system can perform multiplex assays simultaneously with a single sample.

In one particular embodiment, it takes approximately eight minutes for a 10 microliter blood sample to flow through the four measurement zones 209. The start of this analysis may be calculated when the pressure within the channel 206 is approximately −30 kPa. During this time, the optical system 80 is measuring the light transmission for each measurement zone, and in one embodiment, this data may be transmitted to a control system approximately every 0.1 seconds. Using reference values, these measurements may be converted using the following formulas:

$$\text{Transmission} = (l - ld)/(lr - ld) \quad (1)$$

Where:
l = the intensity of transmitted light through a measurement zone at a given point in time
ld = the intensity of transmitted light through a measurement zone with the light source off
lr = a reference intensity (i.e. the intensity of the transmitted light at a measurement zone with the light source activated, or before the start of an analysis when only air is in the channel and $$\text{Optical Density} = -\log(\text{Transmission}) \quad (2)$$

Thus, using these formulas, the optical density in a measurement zone 209 may be calculated.

As described herein, a variety of methods can be used to control fluid flow in a cassette, including the use of pumps, vacuums, valves, and other components associated with an analyzer. In some cases, fluid control can also be performed at least in part by one or more components within the cassette, such as by using a valve positioned within the cassette, or the use of specific fluids and channel configurations with the cassette. In one set of embodiments, control of fluid flow can be achieved based at least in part on the influence of channel geometry and the viscosity of one or more fluids (which may be stored) inside the cassette.

One method includes flowing a plug of a low viscosity fluid and a plug of a high viscosity fluid in a channel including a flow constriction region and a non-constriction region. In one embodiment, the low viscosity fluid flows at a first flow rate in the channel and the flow rate is not substantially affected by the fluid flowing in the flow constriction region. When the high viscosity fluid flows from the non-constriction region to the flow constriction region, the flow rates of the fluids decrease substantially, since the flow rates, in some systems, are influenced by the highest viscosity fluid flowing in the smallest cross-sectional area of the system (e.g., the flow constriction region). This causes the low viscosity fluid to flow at a second, slower flow rate than its original flow rate, e.g., at the same flow rate at which the high viscosity fluid flows in the flow constriction region.

For example, one method of controlling fluid flow may involve flowing a first fluid from a first channel portion to a second channel portion in a microfluidic system, wherein a fluid path defined by the first channel portion has a larger cross-sectional area than a cross-sectional area of a fluid path defined by the second channel portion, and flowing a second fluid in a third channel portion in the microfluidic system in fluid communication with the first and second channel portions, wherein the viscosity of the first fluid is different than the viscosity of the second fluid, and wherein the first and second fluids are substantially incompressible. Without stopping the first or second fluids, a volumetric flow rate of the first and second fluids may be decreased by a factor of at least 3, at least 10, at least 20, at least 30, at least 40, or at least 50 in the microfluidic system as a result of the first fluid flowing from the first channel portion to the second channel portion, compared to the absence of flowing the first fluid from the first channel portion to the second channel portion. A chemical and/or biological interaction involving a component of the first or second fluids may take place at a first measurement zone in fluid communication with the channel portions while the first and second fluids are flowing at the decreased flow rate.

Accordingly, by designing microfluidic systems with flow constriction regions positioned at particular locations and by choosing appropriate viscosities of fluids, a fluid can be made to speed up or slow down at different locations within the system without the use of valves and/or without external control. In addition, the length of the channel portions can be chosen to allow a fluid to remain in a particular area of the system for a certain period of time. Such systems are particularly useful for performing chemical and/or biological assays, as well as other applications in which timing of reagents is important. Non-limiting examples of methods and configurations of channels for controlling fluid flow are described in more detail in U.S. patent application Ser. No. 12/428,372, filed Apr. 22, 2009, published as U.S. Patent Publication No. 2009/0266421, entitled "Flow Control in Microfluidic Systems", which is incorporated herein by reference in its entirety for all purposes.

Any suitable fluid flow source may be used to promote or maintain fluid flow in a microfluidic system or cassette described herein. In some cases, the fluid flow source is part of a microfluidic sample analyzer. A fluid flow source may be configured to pressurize a channel in a cassette to move a sample through the channel In one illustrative embodiment, the fluid flow source is a vacuum system and includes a vacuum source or pump, two vacuum reservoirs which may be separated by a vacuum regulator and a manifold to provide a fluid connection between the vacuum reservoirs and the cassette. The manifold may also include one or more fluid connections to one or more ports on the cassette. For example, the manifold may provide a fluidic connection between a port and a valve (such as a solenoid valve). Opening and closing this valve may control where air can enter the cassette, thus serving as a vent valve in certain embodiments.

As mentioned above, in one embodiment, the vacuum source is a pump, such as a solenoid operated diaphragm pump. In other embodiments, fluid flow may be driven/controlled via use of other types of pumps or sources of fluid flow. For example, in one embodiment, a syringe pump may be used to create a vacuum by pulling the syringe plunger in an outward direction. In other embodiments, a positive pressure is applied to one or more inlets of the cassette to provide a source of fluid flow.

In some embodiments, fluid flow takes place while applying a substantially constant non-zero pressure drop (i.e., AP) across an inlet and an outlet of a cassette. In one set of embodiments, an entire analysis is performed while applying a substantially constant non-zero pressure drop (i.e., AP) across an inlet and an outlet of a cassette. A substantially constant non-zero pressure drop can be achieved, for example, by applying a positive pressure at the inlet or a reduced pressure (e.g., a vacuum) at the outlet. In some cases, a substantially constant non-zero pressure drop is achieved while fluid flow does not take place predominately by capillary forces and/or without the use of actuating valves (e.g., without changing a cross-sectional area of a channel of a fluid path of the cassette). In some embodiments, during essentially the entire analysis conducted in the cassette, a substantially constant non-zero pressure drop may be present across, for example, an inlet to a measurement zone (which may be connected to a fluidic connector) and an outlet downstream of the measurement zone (e.g., an outlet downstream of a liquid containment region), respectively.

In one embodiment, a vacuum source is configured to pressurize a channel to approximately −60 kPa (approximately ⅔ atmosphere). In another embodiment, the vacuum source is configured to pressurize a channel to approximately −30 kPa. In certain embodiments, a vacuum sources is configured to pressurize a channel to, for example, between −100 kPa and −70 kPa, between −70 kPa and −50 kPa, between −50 kPa and −20 kPa, or between −20 kPa and −1 kPa.

As mentioned above, in one embodiment, two vacuum reservoirs may be provided. The pump may be turned on such that the first reservoir may be pressurized to approximately −60 kPa. A regulator positioned between the reservoirs may ensure that the second reservoir may only be pressurized to a different pressure, for example, approximately −30 kPa. This regulator may maintain the pressure of a reservoir at −30 kPa (or at another suitable pressure) as long as the other reservoir remains at a certain pressure range, e.g., between −60 kPa and −30 kPa. Pressure sensors may monitor the pressure within each reservoir. If the pressure in the first reservoir reaches a set point (for example, approximately −40 kPa), the pump may be actuated to decrease the pressure in the first reservoir. The second reservoir may be configured to detect any leaks in the overall vacuum system. Optionally, the vacuum system may include a filter coupled to the reservoirs. A solenoid valve may serve as a vent valve connected through the manifold to a port.

In certain embodiments, once the cassette is positioned within an analyzer, a fluid flow source that is a part of the analyzer may be coupled to the cassette to ensure a fluid-tight connection. For instance, the cassette may include a port configured to couple a channel of the cassette with the fluid source, and optionally to another channel of the cassette. In one embodiment, seals, or o-rings are positioned around the port and a linear solenoid may be positioned above the o-rings to press and seal the o-rings against the cassette body. A manifold adapter may be positioned between the linear solenoid and the manifold, and passive return springs may be provided around the manifold to urge the manifold away from the cassette body when the solenoid is not charged. In one embodiment, multiple ports on the cassette may interface with the manifold. For example, in addition to a port for inserting and/or removing reagents, the cassette may also include one or more venting ports and/or mixing ports. The interface between each port and the manifold may be independent (e.g., there may be no fluidic connection inside the manifold).

In one embodiment, when the fluid flow source is activated, one or more channels in the cassette may be pressurized (e.g., to approximately −30 kPa) which may drive the fluids within the channel (e.g., both fluid sample as well as reagents) toward the outlet. In an embodiment which includes a vent port and a mixing port, a vent valve connected to the vent port through a manifold may initially be open which may enable all of the reagents downstream of the mixing port to move toward the outlet, but will not cause reagents upstream of the mixing port to move. Configurations and uses of vent valves are described in more detail in U.S. Patent Apl. Ser. No. 61/263,981, filed Nov. 14, 2009 and entitled, "Fluid Mixing and Delivery in Microfluidic Systems, which is incorporated herein by reference in its entirety for all purposes. Once the vent valve is closed, reagents upstream of the mixing port may move toward a mixing port and then to the outlet. For example, fluids can be stored serially in a channel upstream of the mixing port, and after closing a vent valve positioned along the channel, the fluids can flow sequentially towards the channel outlet. In some cases, fluids can be stored in separate, intersecting channels, and after closing a vent valve the fluids will flow together toward a point of intersection. This set of embodiments can be used, for example, to controllably mix the fluids as they flow together. The timing of delivery and the volume of fluid delivered can be controlled, for example, by the timing of the vent valve actuation.

Advantageously, vent valves can be operated without constricting the cross-section of the microfluidic channel on which they operate, as might occur with certain valves in the prior art. Such a mode of operation can be effective in preventing leaking across the valve. Moreover, because vent valves can be used, some systems and methods described herein do not require the use of certain internal valves, which can be problematic due to, for example, their high expense, complexity in fabrication, fragility, limited compatibility with mixed gas and liquid systems, and/or unreliability in microfluidic systems.

It should be understood that while vent valves are described, other types of valving mechanisms can be used with the systems and methods described herein. Non-limiting examples of a valving mechanism which may be operatively associated with a valve include a diaphragm valve, ball valve, gate valve, butterfly valve, globe valve, needle valve, pinch valve, poppet valve, or pinch valve. The valving mechanism may be actuated by any suitable means, including a solenoid, a motor, by hand, by electronic actuation, or by hydraulic/pneumatic pressure.

As previously mentioned, all of the liquids in the cassette (e.g., sample and reagents) may move into the liquid containment area which may include an absorbent material. In one embodiment, the absorbent material absorbs only liquids such that gases may flow out of the cassette through the outlet.

A variety of determination (e.g., measuring, quantifying, detecting, and qualifying) techniques may be used, e.g., to analyze a sample component or other component or condition associated with a microfluidic system or cassette described herein. Determination techniques may include optically-based techniques such as light transmission, light absorbance, light scattering, light reflection and visual techniques. Determination techniques may also include luminescence techniques such as photoluminescence (e.g., fluorescence), chemiluminescence, bioluminescence, and/or electrochemiluminescence. In other embodiments, determination techniques may measure conductivity or resistance. As such, an analyzer may be configured to include such and other suitable detection systems.

Different optical detection techniques provide a number of options for determining reaction (e.g., assay) results. In some embodiments, the measurement of transmission or absorbance means that light can be detected at the same wavelength at which it is emitted from a light source. Although the light source can be a narrow band source emitting at a single wavelength it may also may be a broad spectrum source, emitting over a range of wavelengths, as many opaque materials can effectively block a wide range of wavelengths. In some embodiments, a system may be operated with a minimum of optical devices (e.g., a simplified optical detector). For instance, the determining device may be free of a photomultiplier, may be free of a wavelength selector such as a grating, prism or filter, may be free of a device to direct or columnate light such as a columnator, or may be free of magnifying optics (e.g., lenses). Elimination or reduction of these features can result in a less expensive, more robust device.

In one set of embodiments, an optical system is positioned in the housing of an analyzer. As shown illustratively in FIG. 7, an optical system 80 includes at least a first light source 82 and a detector 84 spaced apart from the first light source. The first light source 82 may be configured to pass light through a first measurement zone of the cassette 20 when the cassette is inserted into the analyzer 301. The first detector 84 may be positioned opposite the first light source 82 to detect the amount of light that passes through the first measurement zone of the cassette. In one particular embodiment, the optical system includes ten light sources and ten detectors. It should be appreciated that in other embodiments, the number of light sources and detectors may vary as the invention is not so limited. As described herein, the cassette may include a plurality of measurement zones and the cassette may be positioned within the analyzer such that each measurement zone aligns with a light source and corresponding detector. In some embodiments, the light source includes an optical aperture which may help direct light from the light source to a particular region within a measurement zone of the cassette.

In one embodiment, the light sources are light emitting diodes (LED's) or laser diodes. For example, an InGaAlP red semiconductor laser diode emitting at 654 nm may be used. Other light sources can also be used. The light source may be positioned within a nest or housing. The nest or housing may include a narrow aperture or thin tube that may assist in collimating light. The light sources may be positioned above where the cassette is inserted into the analyzer such that the light source shines down onto the top surface of the cassette. Other suitable configurations of the light source with respect to the cassette are also possible.

It should be appreciated that the wavelength of the light sources may vary as the invention is not so limited. For example, in one embodiment, the wavelength of the light source is approximately 670 nm, and in another embodiment, the wavelength of the light source is approximately 650 nm. It should be appreciated that in one embodiment, the wavelength of each light source may be different such that each measurement zone of the cassette receives a different light wavelength. In one particular embodiment when measuring hemocrit or hemoglobin, an isobestic wavelength range between approximately 590 nm and approximately 805 nm may be used for at least one of the measurement zones.

As mentioned, a detector 84 may be spaced apart from and positioned below a light source to detect the amount of light that passes through the cassette. In one embodiment, one or more of the detectors are photodetectors (e.g., photodiodes). In certain embodiments, the photodetector may be any suitable device capable of detecting the transmission of light that is emitted by the light source. One type of photodetector is an optical integrated circuit (IC) including a photodiode having a peak sensitivity at 700 nm, an amplifier and a voltage regulator. The detector may be positioned within a nest or housing which may include a narrow aperture or thin tube to ensure that only light from the center of the measurement zone is measured at the detector. As described in more detail below, if the light source is pulse modulated, the photodetector may include a filter to remove the effect of light that is not at the selected frequency. When multiple and neighboring signals are detected at the same time, the light source used for each measurement zone (e.g., detection region) can be modulated at a frequency sufficiently different from that of its neighboring light source. In this configuration, the each detector can be configured (e.g., using software) to select for its attributed light source, thereby avoiding interfering light form neighboring optical pairs.

As described herein, a cassette may include a measurement zone which includes a meandering channel configured and arranged to align with a detector such that upon alignment, the detector can measure a single signal through more than one adjacent segment of the meandering channel. In some embodiments, the detector is able to detect a signal within at least a portion of the area of the meandering channel and through more than one segment of the meandering channel such that a first portion of the signal, measured from a first segment of the meandering channel, is similar to a second portion of the signal, measured from a second segment of the meandering channel. In such embodiments, because the signal is present as a part of more than one segment of the meandering channel, there is no need for precise alignment between a detector and a measurement zone.

The positioning of the detector over the measurement zone (e.g., a meandering region) without the need for precision is an advantage, since external (and possibly, expensive) equipment such as microscopes, lenses, and alignment stages are not required (although they may be used in certain embodiments). Instead, alignment may be performed by low-cost methods that do not necessarily require an active or separate alignment step by the user. For example, in one embodiment, a cassette comprising a meandering region can be placed in a slot of an analyzer described herein (e.g., in a cavity having the same or similar shape as the cassette), and the measurement zone can be automatically located in a beam of light of the detector. Possible causes of misalignment caused by, for instance, cassette-to-cassette variations, the exact location of the cassette in the slot, and normal usage of the cassette, may be negligible compared to the dimensions of the measurement zone. As a result, the meandering region can stay within the beam of light and detection is not interrupted due to these variations.

The detector may detect a signal within all, or a portion, of a measurement zone (e.g., including a meandering region). In other words, different amounts of the meandering region may be used as an optical detection pathway. For instance, the detector may detect a signal within at least 15% of the measurement zone, at least 20% of the measurement zone, at least 25% of the measurement zone, within at least 50% of the measurement zone, or within at least 75% of the measurement zone (but less than 100% of the measurement zone). The area in which the measurement zone is used as an optical detection pathway may also depend on, for instance, the opacity of the material in which the channel is fabricated (e.g., whether all, or, a portion, of the channel is transparent), the amount of a non-transparent material that may cover a portion of the channel (e.g., via use of a protective cover), and/or the size of the detector and the measurement zone.

In one embodiment, a signal produced by a reaction carried out in the cassette is homogenous over the entire measurement zone (e.g., over an entire meandering channel region). That is, the measurement zone (e.g., meandering channel region) may allow production and/or detection of a single, homogenous signal in said region upon carrying out a chemical and/or biological reaction (e.g., and upon detection by a detector). Prior to carrying out a reaction in the meandering channel region, the meandering channel may include, for example, a single species (and concentration of species) to be detected/determined. The species may be adsorbed to a surface of the meandering channel. In another embodiment, the signal may be homogeneous over only portions of the meandering region, and one or more detectors may detect different signals within each of the portions. In certain instances, more than one measurement zone can be connected in series and each measurement zone can be used to detect/determine a different species. It should be understood that while meandering regions are described, measurement zones that do not include meandering regions can also be used.

Applicant has recognized that the amount of light transmitted through a measurement zone of the cassette may be used to determine information about not only the sample, but also information about specific processes occurring in the fluidic system of the cassette (e.g., mixing of reagents, flow rate, etc.). In some cases, measurement of light through a region can be used as feedback to control fluid flow in the system, as described herein.

In some cases, optical density of a fluid is determined It should be recognized that a clear liquid (such as water) may allow a large amount of light to be transmitted from the light source, through a measurement zone and to a detector. Air within the measurement zone may lead to less light transmitted through the measurement zone because more light may scatter within the channel compared to when a clear liquid is present. When a blood sample is in a measurement zone, a significantly less amount of light may pass through to the detector due to the light scattering off of blood cells and also due to absorbance. In one embodiment, silver associates with a sample component bound to a surface within the measurement zone and as silver builds up within the measurement zone, less and less light is transmitted through the measurement zone.

It is recognized that measuring the amount of light that is detected at each detector enables a user to determine which reagents are in a particular measurement zone at a particular point in time. It is also recognized that by measuring the amount of light that is detected with each detector, it is possible to measure the amount of silver deposited in each measurement zone. This amount may correspond to the amount of analyte captured during a reaction which may thus provide a measure of the concentration of the analyte in the sample.

As described herein, Applicant has recognized that an optical system may be used for a variety of quality control reasons. First, the time it takes for a sample to reach a measurement zone where the optical system detects the light that passes though the measurement zone may be used to determine whether there is a leak or clog in the system. Also, when the sample is expected to be a certain volume, for example, approximately 10 microliters, there is an expected flow time which would be associated for the sample to pass through the channels and measurement zones. If the sample falls outside of that expected flow time, it could be an indication that there is not enough sample to conduct the analysis and/or that the wrong type of sample was loaded into the analyzer. Additionally, an expected range of results may be determined based upon the type of sample (e.g., serum, blood, urine, etc.) and if the sample is outside of the expected range, it could be an indication of an error.

In one embodiment, an optical system includes a plurality of light sources and a plurality of corresponding detectors. In one embodiment, a first light source is adjacent a second light source, where the first light source is configured to pass light though a first measurement zone of a cassette and the second light source is configured to pass light through a second measurement zone of the cassette. In one embodiment, the light sources are configured such that the second light source is not activated unless the first light source is deactivated. Applicant has recognized that some light from one light source may spread over to an adjacent detector and may affect the amount of light detected at the adjacent detector. In one set of embodiments, if the adjacent light source is activated at the same time as the first light source, then both detectors are also measuring the amount of light that passes through the first and second measurement zones of the cassette at the same time, which may lead to inaccurate measurements.

Thus, in one set of embodiments, the plurality of light sources are configured to activate sequentially with only one light source activated at a time. The corresponding detector for the activated light source is thus only detecting the amount of light that passes through the corresponding measurement zone. In one particular embodiment, the light sources are configured to each activate for a short period of time (e.g., at least approximately 500, 250, 100, or 50 microseconds, or, in some embodiments, less than or equal to approximately 500, 250, 100, or 50 microseconds), and then an adjacent light source is configured to activate for a similar time frame. Activation for 100 microseconds corresponds to a rate of 10 kHz. In one embodiment, a multiplexed analog to digital converter is used to pulse the light and measure the amount of light detected at each corresponding detector every 500, 250, 100, or 50 microseconds. Pulsing the light in this manner may help to prevent stray light passing through one measurement zone to alter the amount of light detected that passes through an adjacent measurement zone.

Although there may be some benefits associated with pulsing the light sources in the manner described above, it should be recognized that the invention is not so limited and that other arrangements may be possible, such as where multiple light sources may be activated at the same time. For example, in one embodiment, light sources that are not directly adjacent to one another can be activated substantially simultaneously.

In one embodiment, an analyzer includes a temperature regulating system positioned within the housing which may be configured to regulate the temperature within the analyzer. For certain sample analysis, the sample may need to be kept within a certain temperature range. For example, in one embodiment, it is desirable to maintain the temperature within the analyzer at approximately 37° C. Accordingly, in one embodiment, the temperature regulating system includes a heater configured to heat the cassette. In one embodiment, the heater is a resistive heater which may be positioned on the underside of where the cassette is placed in the analyzer. In one embodiment, the temperature regulating system also includes a thermistor to measure the temperature of the cassette and a controller circuit may be provided to control the temperature.

In one embodiment, the passive flow of air within the analyzer may act to cool the air within the analyzer if needed. A fan (not shown) may optionally be provided in the analyzer to lower the temperature within the analyzer. In some embodiments, the temperature regulating system may include Peltier thermoelectric heaters and/or coolers within the analyzer.

In certain embodiments, an identification system including one or more identifiers is used and associated with one or more components or materials associated with a cassette and/or analyzer. The "identifiers," as described in greater detail below, may themselves be "encoded with" information (i.e. carry or contain information, such as by use of an information carrying, storing, generating, or conveying device such as a radio frequency identification (RFID) tag or bar code) about the component including the identifier, or may not themselves be encoded with information about the component, but rather may only be associated with information that may be contained in, for example, a database on a computer or on a computer readable medium (e.g., information about a user, and/or sample to be analyzed). In the latter instance, detection of such an identifier can trigger retrieval and usage of the associated information from the database.

Identifiers "encoded with" information about a component need not necessarily be encoded with a complete set of information about the component. For example, in certain embodiments, an identifier may be encoded with information merely sufficient to enable a unique identification of the cassette (e.g. relating to a serial no., part no., etc.), while additional information relating to the cassette (e.g. type, use (e.g., type of assay), ownership, location, position, connectivity, contents, etc.) may be stored remotely and be only associated with the identifier.

"Information about" or "information associated with" a cassette, material, or component, etc. is information regarding the identity, positioning, or location of the cassette, material or component or the identity, positioning, or location of the contents of a cassette, material or component and may additionally include information regarding the nature, state or composition of the cassette, material, component or contents. "Information about" or "information associated with" a cassette, material or component or its contents can include information identifying the cassette, material or component or its contents and distinguishing the cassette, material, component or its contents from others. For example, "information about" or "information associated with" a cassette, material or component or its contents may refer to information indicating the type or what the cassette, material or component or its contents is, where it is or should be located, how it is or should be positioned, the function or purpose of the cassette, material or component or its contents, how the cassette, material or component or its contents is to be connected with other components of the system, the lot number, origin, calibration information, expiration date, destination, manufacturer or ownership of the cassette, material or component or its contents, the type of analysis/assay to be performed in the cassette, information about whether the cassette has been used/analyzed, etc.

In one set of embodiments, an identifier is associated with a cassette and/or analyzer described herein. In general, as used herein, the term "identifier" refers to an item capable of providing information about the cassette and/or analyzer (e.g. information including one or more of identity, location, or position/positioning of the cassette and/or analyzer or a component thereof) with which the identifier is associated or installed into, or capable of being identified or detected and the identification or detection event being associated with information about the cassette and/or analyzer with which the identifier is associated. Non-limiting examples of identifiers that may be used in the context of the invention include radio frequency identification (RFID) tags, bar codes, serial numbers, color tags, fluorescent or optical tags (e.g., using quantum dots), chemical compounds, radio tags, magnetic tags, among others.

In one embodiment, an analyzer may include an identification reader positioned within the housing configured to read information about with the cassette. Any suitable identification reader that can be used to read information from an identifier. Non-limiting examples of identification readers include RFID readers, bar code scanners, chemical detectors, cameras, radiation detectors, magnetic or electric field detectors, among others. The method of detection/reading and appropriate type of identification detector depends on the particular identifier utilized and can include, for example, optical imaging, fluorescence excitation and detection, mass spectrometry, nuclear magnetic resonance, sequencing, hybridization, electrophoresis, spectroscopy, microscopy, etc. In some embodiments, the identification readers may be mounted or pre-embedded in specific locations (e.g., on or within a cassette and/or analyzer).

In one embodiment, the identification reader is an RFID reader configured to read an RFID identifier associated with the cassette. For example, in one embodiment, the analyzer includes an RFID module and antenna that are configured to read information from the cassette inserted into the analyzer. In another embodiment, the identification reader is a barcode reader configured to read a barcode associated with the cassette. Once the cassette is inserted into the analyzer, the identification reader may read the information from the cassette. The identifier on the cassette may include one or more of the types of information such as cassette type, type of analysis/assay to be performed, lot number, information about whether the cassette has been used/analyzed, and other information described herein. The reader may also be configured to read information provided with a group of cassettes, such as in a box of cassettes, such as, but not limited to calibration information, expiration date, and any additional information specific to that lot. The information identified may be optionally displayed to a user, e.g., to confirm that a correct cassette and/or type of assay is being performed.

In some cases, the identification reader may be integrated with a control system via communication pathways. Communication between the identification readers and the control system may occur along a hard-wired network or may be transmitted wirelessly. In one embodiment, the control system can be programmed to recognize a specific identifier (e.g., of a cassette associated with information relating to a cassette type, manufacturer, assay to be performed, etc.) as indicating the cassette is suitably connected or inserted within a particular type of analyzer.

In one embodiment, the identifier of a cassette be associated with predetermined or programmed information contained in a database regarding the use of the system or cassette for a particular purpose, user or product, or with particular reaction conditions, sample types, reagents, users, and the like. If an incorrect match is detected or an identifier has been deactivated, the process may be halted or the system may be rendered not operable until the user has been notified, or upon acknowledgement by a user.

The information from or associated with an identifier can, in some embodiments, be stored, for example in computer memory or on a computer readable medium, for future reference and record-keeping purposes. For example, certain control systems may employ information from or associated with identifiers to identify which components (e.g., cassettes) or type of cassettes were used in a particular analysis, the date, time, and duration of use, the conditions of use, etc. Such information may be used, for example, to determine whether one or more components of the analyzer should be cleaned or replaced. Optionally, a control system or any other suitable system could generate a report from gathered information, including information encoded by or associated with the identifiers, that may be used in providing proof of compliance with regulatory standards or verification of quality control.

Information encoded on or associated with an identifier may also be used, for example, to determine whether the component associated with the identifier (e.g., a cassette) is authentic or counterfeit. In some embodiments, the determination of the presence of a counterfeit component causes system lockout. In one example, the identifier may contain a unique identity code. In this example, the process control software or analyzer would not permit system startup (e.g., the system may be disabled) if a foreign or mismatched identity code (or no identity code) was detected.

In certain embodiments, the information obtained from or associated with an identifier can be used to verify the identity of a customer to whom the cassette and/or analyzer is sold or for whom a biological, chemical, or pharmaceutical process is to be performed. In some cases, the information obtained from or associated with an identifier is used as part of a process of gathering data for troubleshooting a system. The identifier may also contain or be associated with information such as batch histories, assembly process and instrumentation diagrams (P and IDs), troubleshooting histories, among others. Troubleshooting a system may be accomplished, in some cases, via remote access or include the use of diagnostic software.

In one embodiment, an analyzer includes a user interface, which may be positioned within the housing and configured for a user to input information into the sample analyzer. In one embodiment, the user interface includes a touch screen. The touch screen may guide a user through the operation of the analyzer, providing text and/or graphical instructions for use of the analyzer. The user interface may guide the user to input the patient's name or other patient identification source/number into the analyzer. Any suitable patient information such as name, date of birth, and/or patient ID number may be inputted into the touch screen user interface to identify the patient. The user interface may indicate the amount of time remaining to complete the analysis of the sample.

Figure 8:
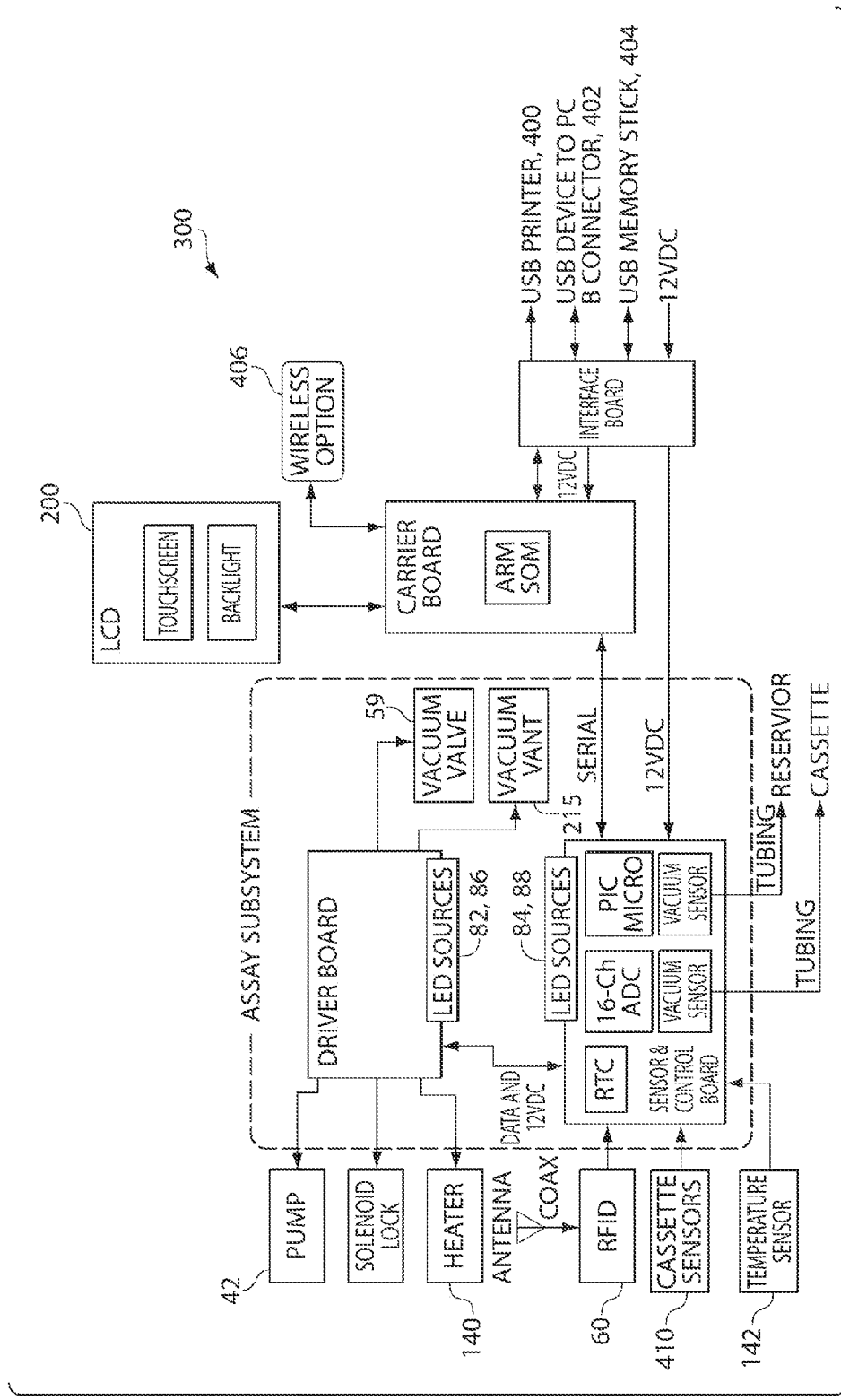
FIG. 8 is a block diagram showing a control system of a sample analyzer associated with a variety of different components according to one embodiment.

In another embodiment, the user interface may be configured differently, such as with an LCD display and a single button scroll through menu. In another embodiment, the user interface may simply include a start button to activate the analyzer. In other embodiments, the user interface from separate independent devices (such as a smart phone or mobile computer) can be used to interface with the analyzer. FIG. 8 is a block diagram 300 that illustrates how a control system 305 (see FIG. 7) may be operatively associated with a variety of different components according to one embodiment. Control systems described herein can be implemented in numerous ways, such as with dedicated hardware or firmware, using a processor that is programmed using microcode or software to perform the functions recited above or any suitable combination of the foregoing. A control system may control one or more operations of a single analysis (e.g., for a biological, biochemical or chemical reaction), or of multiple (separate or interconnected) analyses. As shown illustratively in FIG. 7, control system 305 may be positioned within the housing 101 of the analyzer and may be configured to communicate with the identification reader 60, the user interface 200, the fluid flow source 40, the optical system 80, and/or the temperature regulating system to analyze a sample in the cassette.

In one embodiment, the control system includes at least two processors, including a real time processor that controls and monitors all of the sub-systems which directly interface with the cassette. In one embodiment, at a particular time interval (e.g., every 0.1 seconds), this processor communicates with a second higher level processor which communicates with the user through the user interface and/or the communication sub-system (discussed below) and directs the operation of the analyzer (e.g., determines when to start analyzing a sample and interprets the results). In one embodiment, communication between these two processors occurs through a serial communication bus. It should be appreciated that in another embodiment, the analyzer may only include one processor, or more than two processors, as the invention is not so limited.

In one embodiment, the analyzer is capable of interfacing with external devices and may, for example, include ports for connection with one or more external communication units. External communication may be accomplished, for example, via USB communication. For example, as shown illustratively in FIG. 8, the analyzer may output the results of a sample analysis to a USB printer 400, or to a computer 402. Additionally, the data stream produced by the real time processor may be outputted to a computer or a USB memory stick 404. In some embodiments, a computer may be able to directly control the analyzer through a USB connection as well. Further, other types of communication options are available as the present invention is not limited in this respect. For example, Ethernet, Bluetooth and/or WI-FI communication 406 with the analyzer may be established through the processor.

The calculation methods, steps, simulations, algorithms, systems, and system elements described herein may be implemented using a computer implemented control system, such as the various embodiments of computer implemented systems described below. The methods, steps, systems, and system elements described herein are not limited in their implementation to any specific computer system described herein, as many other different machines may be used.

The computer implemented control system can be part of or coupled in operative association with a sample analyzer, and, in some embodiments, configured and/or programmed to control and adjust operational parameters of the sample analyzer, as well as analyze and calculate values, as described above. In some embodiments, the computer implemented control system can send and receive reference signals to set and/or control operating parameters of the sample analyzer and, optionally, other system apparatus. In other embodiments, the computer implemented system can be separate from and/or remotely located with respect to the sample analyzer and may be configured to receive data from one or more remote sample analyzer apparatus via indirect and/or portable means, such as via portable electronic data storage devices, such as magnetic disks, or via communication over a computer network, such as the Internet or a local intranet.

A computer implemented control system may include several known components and circuitry, including a processing unit (i.e., processor), a memory system, input and output devices and interfaces (e.g., an interconnection mechanism), as well as other components, such as transport circuitry (e.g., one or more busses), a video and audio data input/output (I/O) subsystem, special-purpose hardware, as well as other components and circuitry, as described below in more detail. Further, the computer system may be a multi-processor computer system or may include multiple computers connected over a computer network.

The computer implemented control system may include a processor, for example, a commercially available processor such as one of the series x86, Celeron and Pentium processors, available from Intel, similar devices from AMD and Cyrix, the 680X0 series microprocessors available from Motorola, and the PowerPC microprocessor from IBM. Many other processors are available, and the computer system is not limited to a particular processor.

A processor typically executes a program called an operating system, of which WindowsNT, Windows 95 or 98, UNIX, Linux, DOS, VMS, MacOS and OS8 are examples, which controls the execution of other computer programs and provides scheduling, debugging, input/output control, accounting, compilation, storage assignment, data management and memory management, communication control and related services. The processor and operating system together define a computer platform for which application programs in high-level programming languages are written. The computer implemented control system is not limited to a particular computer platform.

The computer implemented control system may include a memory system, which typically includes a computer readable and writeable non-volatile recording medium, of which a magnetic disk, optical disk, a flash memory and tape are examples. Such a recording medium may be removable, for example, a floppy disk, read/write CD or memory stick, or may be permanent, for example, a hard drive.

Such a recording medium stores signals, typically in binary form (i.e., a form interpreted as a sequence of one and zeros). A disk (e.g., magnetic or optical) has a number of tracks, on which such signals may be stored, typically in binary form, i.e., a form interpreted as a sequence of ones and zeros. Such signals may define a software program, e.g., an application program, to be executed by the microprocessor, or information to be processed by the application program.

The memory system of the computer implemented control system also may include an integrated circuit memory element, which typically is a volatile, random access memory such as a dynamic random access memory (DRAM) or static memory (SRAM). Typically, in operation, the processor causes programs and data to be read from the non-volatile recording medium into the integrated circuit memory element, which typically allows for faster access to the program instructions and data by the processor than does the non-volatile recording medium.

The processor generally manipulates the data within the integrated circuit memory element in accordance with the program instructions and then copies the manipulated data to the non-volatile recording medium after processing is completed. A variety of mechanisms are known for managing data movement between the non-volatile recording medium and the integrated circuit memory element, and the computer implemented control system that implements the methods, steps, systems and system elements described above in relation to FIG. 8 is not limited thereto. The computer implemented control system is not limited to a particular memory system.

At least part of such a memory system described above may be used to store one or more data structures (e.g., look-up tables) or equations described above. For example, at least part of the non-volatile recording medium may store at least part of a database that includes one or more of such data structures. Such a database may be any of a variety of types of databases, for example, a file system including one or more flat-file data structures where data is organized into data units separated by delimiters, a relational database where data is organized into data units stored in tables, an object-oriented database where data is organized into data units stored as objects, another type of database, or any combination thereof.

The computer implemented control system may include a video and audio data I/O subsystem. An audio portion of the subsystem may include an analog-to-digital (A/D) converter, which receives analog audio information and converts it to digital information. The digital information may be compressed using known compression systems for storage on the hard disk to use at another time. A typical video portion of the I/O subsystem may include a video image compressor/decompressor of which many are known in the art. Such compressor/decompressors convert analog video information into compressed digital information, and vice-versa. The compressed digital information may be stored on hard disk for use at a later time.

The computer implemented control system may include one or more output devices. Example output devices include a cathode ray tube (CRT) display, liquid crystal displays (LCD) and other video output devices, printers, communication devices such as a modem or network interface, storage devices such as disk or tape, and audio output devices such as a speaker.

The computer implemented control system also may include one or more input devices. Example input devices include a keyboard, keypad, track ball, mouse, pen and tablet, communication devices such as described above, and data input devices such as audio and video capture devices and sensors. The computer implemented control system is not limited to the particular input or output devices described herein.

It should be appreciated that one or more of any type of computer implemented control system may be used to implement various embodiments described herein. Aspects of the invention may be implemented in software, hardware or firmware, or any combination thereof. The computer implemented control system may include specially programmed, special purpose hardware, for example, an application-specific integrated circuit (ASIC). Such special-purpose hardware may be configured to implement one or more of the methods, steps, simulations, algorithms, systems, and system elements described above as part of the computer implemented control system described above or as an independent component.

The computer implemented control system and components thereof may be programmable using any of a variety of one or more suitable computer programming languages. Such languages may include procedural programming languages, for example, C, Pascal, Fortran and BASIC, object-oriented languages, for example, C++, Java and Eiffel and other languages, such as a scripting language or even assembly language.

The methods, steps, simulations, algorithms, systems, and system elements may be implemented using any of a variety of suitable programming languages, including procedural programming languages, object-oriented programming languages, other languages and combinations thereof, which may be executed by such a computer system. Such methods, steps, simulations, algorithms, systems, and system elements can be implemented as separate modules of a computer program, or can be implemented individually as separate computer programs. Such modules and programs can be executed on separate computers.

Such methods, steps, simulations, algorithms, systems, and system elements, either individually or in combination, may be implemented as a computer program product tangibly embodied as computer-readable signals on a computer-readable medium, for example, a non-volatile recording medium, an integrated circuit memory element, or a combination thereof. For each such method, step, simulation, algorithm, system, or system element, such a computer program product may comprise computer-readable signals tangibly embodied on the computer-readable medium that define instructions, for example, as part of one or more programs, that, as a result of being executed by a computer, instruct the computer to perform the method, step, simulation, algorithm, system, or system element.

It should be appreciated that various embodiments may be formed with one or more of the above-described features. The above aspects and features may be employed in any suitable combination as the present invention is not limited in this respect. It should also be appreciated that the drawings illustrate various components and features which may be incorporated into various embodiments. For simplification, some of the drawings may illustrate more than one optional feature or component. However, the invention is not limited to the specific embodiments disclosed in the drawings. It should be recognized that the invention encompasses embodiments which may include only a portion of the components illustrated in any one drawing figure, and/or may also encompass embodiments combining components illustrated in multiple different drawing figures.

EXAMPLES

The following example is intended to illustrate certain embodiments of the present invention, but do not exemplify the full scope of the invention.

Example 1

Figure 9:
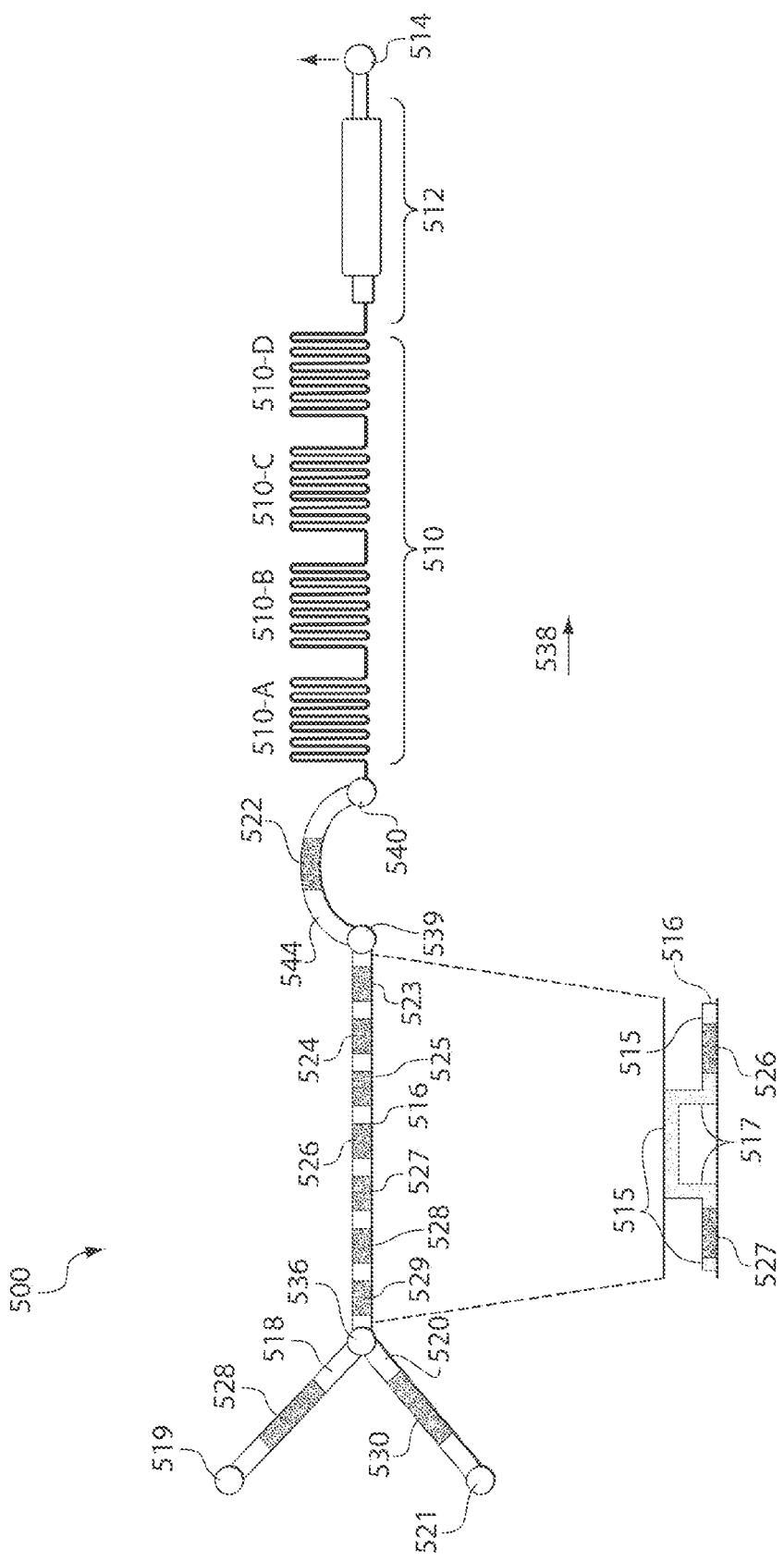
FIG. 9 is a schematic diagram showing a microfluidic system of a cassette according to one embodiment.

This example describes the use of a cassette and analyzer to perform an assay to detect PSA in a sample by electrolessly depositing silver onto gold particles that are associated with the sample. FIG. 9 includes a schematic illustration of a microfluidic system 500 of a cassette used in this example. The cassette had a similar shape to cassette 20 shown in FIG. 3. The microfluidic system used in this example is generally described in International Patent Publication No. WO2005/066613 (International Patent Application Serial No. PCT/US2004/043585), filed Dec. 20, 2004 and entitled "Assay Device and Method," which is incorporated herein by reference in its entirety for all purposes.

The microfluidic system included measurement zones 510A-510D, waste containment region 512, and an outlet 514. The measurement zones included a microfluidic channel 50 microns deep and 120 microns wide, with a total length of 175 mm The microfluidic system also included microfluidic channel 516 and channel branches 518 and 520 (with inlets 519 and 521, respectively). Channel branches 518 and 520 were 350 microns deep and 500 microns wide. Channel 516 was formed of sub-channels 515, which were 350 microns deep and 500 microns wide located on alternating sides of the cassette, connected by through holes 517 having a diameter of approximately 500 microns. Although FIG. 9 shows that reagents were stored on a single side of the cassette, in other embodiments, reagents were stored on both sides of the cassette. Channel 516 had a total length of 390 mm, and branches 518 and 520 were each 360 mm long. Before sealing the channels, anti-PSA antibodies were attached to a surface of the microfluidic system in a segment of the measurement zone 510.

Prior to first use, the microfluidic system was loaded with liquid reagents which were stored in the cassette. A series of 7 wash plugs 523-529 (either water of buffer, approximately 2 microliters each) were loaded using a pipette into sub-channels 515 of channel 516 using the thru-holes. Each of the wash plugs was separated by plugs of air. Fluid 528, containing a solution of silver salt, was loaded into branching channel through port 519 using a pipette. Fluid 530, containing a reducing solution, was loaded into branching channel 520 through port 521. Each of the liquids shown in FIG.9 were separated from the other liquids by plugs of air. Ports 514, 519, 521, 536, 539, and 540 were sealed with an adhesive tape that can be easily removed or pierced. As such, the liquids were stored in the microfluidic system prior to first use.

At first use, the ports 514, 519, 521, 536, 539, and 540 were unsealed by a user peeling off a tape covering the opening of the ports. A tube 544 containing lyophilized anti-PSA antibodies labeled with colloidal gold and to which 10 microliters of sample blood (522) was added, was connected to ports 539 and 540. The tube was part of a fluid connector having a shape and configuration shown in FIG. 3. This created a fluidic connection between measurement zone 510 and channel 516, which were otherwise unconnected and not in fluid communication with one another prior to first use.

The cassette including microfluidic system 500 was inserted into an opening of an analyzer (e.g., as shown in FIG. 7). The housing of the analyzer included an arm positioned within the housing that was configured to engage a cammed surface on the cassette. The arm extended at least partially into the opening in the housing such that as the cassette was inserted into the opening, the arm was pushed away from the opening into a second position allowing the cassette to enter the opening. Once the arm engaged the inwardly cammed surface of the cassette, the cassette was positioned and retained within the housing of the analyzer, and the bias of the spring prevented the cassette from slipping out of the analyzer. The analyzer senses the cassette's insertion by means of a position sensor.

An identification reader (RFID reader) positioned within the housing of the analyzer was used to read an RFID tag on the cassette which includes lot identification information. The analyzer used this identifier to match lot information (e.g., calibration information, expiration date of the cassette, verification that the cassette is new, and the type of analysis/assay to be performed in the cassette) stored in the analyzer. The user was prompted to input information about the patient (from which the sample was acquired) into the analyzer using the touch screen. After the information about the cassette was verified by the user, the control system initiated the analysis.

The control system included programmed instructions to perform the analysis. To initiate the analysis, a signal was sent to the electronics controlling a vacuum system, which was a part of the analyzer and used to provide fluid flow. A manifold with o-rings was pressed against the cassette surface by a solenoid. One port on the manifold sealed (by an o-ring) to port 536 of the microfluidic system of the cassette. This port on the manifold was connected by a tube to a simple solenoid valve (SMC V124A-6G-M5, not shown) which was open to the atmosphere. A separate vacuum port on the manifold sealed (by-o-ring) to port 514 of the microfluidic system of the cassette. A vacuum of approximately −30 kPa was applied to port 514. Throughout the analysis, the channel including measurement zone 510 positioned between ports 540 and 514 had a substantially constant non-zero pressure drop of approximately −30 kPa. Sample 522 was flowed in the direction of arrow 538 into each of measurement zones 510A-510D. As the fluid passed through the measurement zones, the PSA proteins in sample 522 were captured by anti-PSA antibodies immobilized on the measurement zone walls, as described in more detail below. The sample took about 7-8 minutes to pass through the measurement zone, after which it was captured in the waste containment region 512.

Initiation of the analysis also involved the control system sending a signal to the optical detectors, which were positioned adjacent each of measurement zones 510, to initiate detection. Each of the detectors associated with the measurement zones recorded the transmission of light through the channels of the measurement zones, as shown in a plot 600 illustrated in FIG. 10. As the sample passed by each of the measurement zones, peaks 610A-610D were produced. The peaks (and troughs) measured by the detectors are signals (or are converted to signals) that are sent to the control system which compared the measured signals to reference signals or values pre-programmed into the control system. The control system included a pre-programmed set of instructions for providing feedback to the microfluidic system based at least in part on the comparison of signals/values.

In a first measurement zone 510-A of device 500 of FIG. 9, the walls of the channel of this measurement zone were blocked with a blocking protein (Bovine Serum Albumin) prior to first use (e.g., prior to sealing the device). Little or no proteins in the blood sample attached to the walls of the measurement zone 510-A (except for perhaps some non-specific binding which may be washed off). This first measurement zone acted as a negative control.

In a second measurement zone 510-B, the walls of the channel of this measurement zone were coated with a predetermined large quantity of a prostate specific antigen (PSA) prior to first use (e.g., prior to sealing the device) to act as a high or positive control. As the blood sample passed through the second measurement zone 510-B, little or no PSA proteins in the blood bound to the walls of the channel. Gold conjugated signal antibodies in the sample may not yet be bound to the PSA in the sample, and thus they may bind to the PSA on the walls of the channel to act as a high or positive control.

In a third measurement zone 510-C, the walls of the channel of this measurement zone were coated with a predetermined low quantity of PSA prior to first use (e.g., prior to sealing the device) to act as a low control. As the blood sample flowed through this measurement zone, little or no PSA proteins in the sample bind to the wall of the channel Gold conjugated signal antibodies in the sample may bind to the PSA on the walls of the channel to act as a low control.

In a fourth measurement zone 510-D, the walls of the channel of this measurement zone were coated with the capture antibody, an anti-PSA antibody, which binds to a different epitope on the PSA protein than the gold conjugated signal antibody. The walls were coated prior to first use (e.g., prior to sealing the device). As the blood sample flowed through the fourth measurement zone during use, PSA proteins in the blood sample bound to the anti-PSA antibody in a way that is proportional to the concentration of these proteins in the blood. Since the sample, which included PSA, also included gold-labeled anti-PSA antibodies coupled to the PSA, the PSA captured on the measurement zone walls formed a sandwich immunocomplex.

Wash fluids 523-529 followed the sample through the measurement zones 510 towards waste containment region 512 in the direction of arrow 538. As the wash fluids were passed through the measurement zones, they washed away remaining unbound sample components. Each wash plug cleaned the channels of the measurement zones, providing progressively more complete cleaning. The last wash fluid 529 (water) washed away salts that could react with silver salts (e.g., chloride, phosphate, azide).

Figure 10:
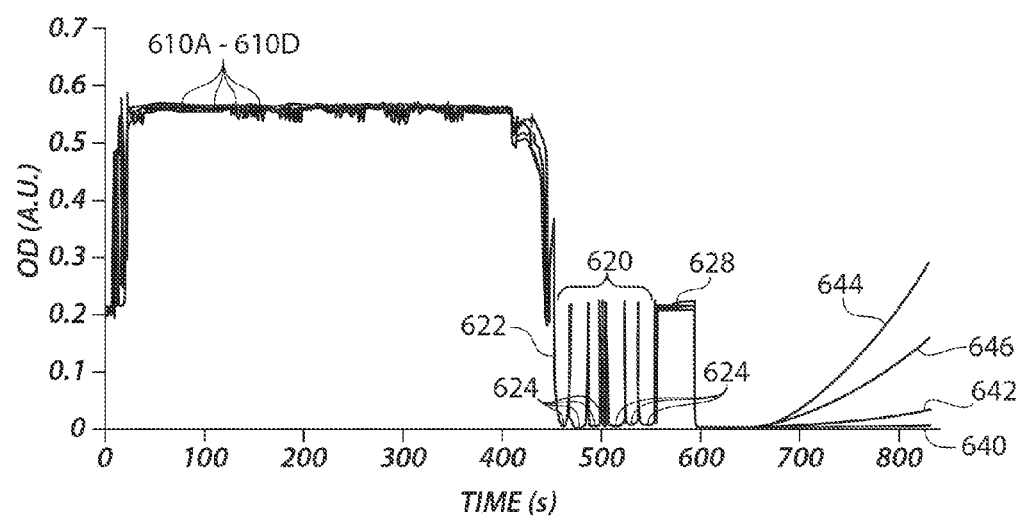
FIG. 10 is a plot showing measurement of optical density as a function of time according to one embodiment.

As shown in the plot illustrated in FIG. 10, while the wash fluids were flowing through the measurement zones, each of the detectors associated with the measurement zones measures a pattern 620 of peaks and troughs. The troughs corresponded to the wash plugs (which are clear liquids and thus provide maximum light transmission). The peaks between each plug represent the air between each plug of clear liquid. Since the assay included 7 wash plugs, 7 troughs and 7 peaks are present in plot 600. The first trough 622 is generally not as deep as the other troughs 624 since the first wash plug often catches blood cells left in the channel and thus is not completely clear.

The final peak of air 628 is much longer than the previous peaks because there were no wash plugs to follow. As a detector detects the length of this air peak, one or more signals is sent to the control system which compares the length of time of this peak to a pre-set reference signal or input value having a particular length. If the length of time of the measured peak is long enough compared to the reference signal, the control system sends a signal to the electronics controlling vent valve 536 to actuate the valve and initiate mixing of fluids 528 and 530. (Note that the signal of peak of air 628 may be combined with a signal indicating either 1) the intensity of the peak; 2) where this peak is positioned as a function of time, and/or 3) one or more signals indicating that a series of peaks 620 of particular intensity has already passed. In this way, the control system distinguishes peak of air 628 from other peaks of long duration such as peak 610 from the sample, e.g., using a pattern of signals.)

To initiate mixing, the solenoid connected by the manifold to vent port 536 is closed. Since the vacuum remains on and no air can enter through vent valve 536, air enters the device through ports 519 and 521 (which are open). This forces the two fluids 528 and 530 in the two storage channels upstream of vent valve 536 to move substantially simultaneously toward outlet 514. These reagents mix at the intersection of the channels to form an amplification reagent (a reactive silver solution) having a viscosity of about $1 \times 10^{-3}$ Pa·s. The ratio of the volumes of fluids 528 and 530 was about 1:1. The amplification reagent continued through the downstream storage channel, through tube 544, through measurement zones 510, and then to waste containment region 512. After a set amount of time (12 seconds), the analyzer reopened vent valve 536 such that air flows through vent valve 536 (instead of the vent ports). This left some reagent behind in the upstream storage channels 518 and 520 on the device. This also results in a single plug of mixed amplification reagent. The 12 seconds of vent-valve closure results in an amplification plug of approximately 50 µL. (Instead of simple timing, another way to trigger the re-opening of the vent valve would be to detect the amplification reagent as it first enters the measurement zones.)

Because the mixed amplification reagent is stable for only a few minutes (usually less than 10 minutes), the mixing was performed less than a minute before use in measurement zone 510. The amplification reagent is a clear liquid, so when it enters the measurement zones, optical density is at its lowest. As the amplification reagent passed across the measurement zones, silver was deposited on the captured gold particles to increase the size of the colloids to amplify the signal. (As noted above, gold particles were present in the low and high positive control measurement zones and, to the extent that PSA was present in the sample, in the test measurement zone.) Silver can then be deposited on top of the already deposited silver, leaving more and more silver deposited in the measurement zones. Eventually the deposited silver reduces the transmission of light through the measurement zones. The reduction in transmitted light is proportional to the amount of silver deposited and can be related to the amount of gold colloids captured on the channel walls. In a measurement zone where no silver is deposited (the negative control for example, or the test area when the sample contains none of the target protein, such as PSA), there will be no (or minimal) increase in optical density. In a measurement zone with significant silver deposition, the slope and ultimate level of the pattern of increasing optical density will be high. The analyzer monitors the pattern of this optical density during amplification in the test area to determine the concentration of analyte in the sample. In one version of the test, the pattern is monitored within the first three minutes of amplification. The optical density in each of the measurement zones as a function of time was recorded and are shown as curves 640, 644, 642, and 646 in FIG. 10. These curves corresponded to signals that were produced in measurement zones 510-A, 510-B, 510-C, and 510-D, respectively.

After three minutes of amplification, the analyzer stops the test. No more optical measurements are recorded and the manifold is disengaged from the device. The test result is displayed on the analyzer screen and communicated to a printer, computer, or whatever output the user has selected. The user may remove the device from the analyzer and throw it away. The sample and all the reagents used in the assay remain in the device. The analyzer is ready for another test.

It should be noted that the control of the flow rates of the fluids within channel 516 and the measurement zone 510 were important when flowing fluids through the system. Due to the measurement zone's relatively small cross sectional area, it served as a bottleneck, controlling the overall flow rate in the system. When the measurement zone contained liquids, the linear flow rates of the fluids in channel 516 was about 0.5 mm s$^{-1}$. Fluids flowing from branching channels 518 and 520 into main channel 516 might not have mixed reproducibly at this rate, as one fluid might have flowed faster than the other, causing unequal portions of fluids 528 and 530 to be mixed. On the other hand, when the measurement zone contained air, the linear flow rates of the fluids in channel 516 and branching channels 518 and 520 were about 15 mm s$^{-1}$. At this higher flow rate, the flow rate in branching channels 518 and 520 were equal and reproducible (when vent valve 536 was closed), producing reproducible mixing. For this reason, the valve connected to port 536 was not closed until fluid 542 passed through the measurement zone to the waste containment region. As noted above, determination of when fluid 542 had exited the measurement zone 510 was performed using an optical detector so as to measure transmission of light through part of measurement zone 510 in combination with a feedback system.

The microfluidic system shown in FIG. 9 was designed such that the volume of the channel between vent valve 536 and measurement zone 510 was larger than the expected volume of the mixed activated silver solution (i.e., the combined portion of fluids 528 and 530 which traveled into channel 516 while vent valve 536 was closed). This ensured that substantially all of the mixing took place at a relatively high linear flow rate (since no liquid, and only air, was present in the measurement zone 510 at this time), and before the activated solution reached the measurement zone. This configuration helped promote reproducible and equal mixing. For the assay described in this example, it was important to sustain a flow of the activated silver mixture within the measurement zone for a few minutes (e.g., 2 to 10 minutes).

This example shows that analysis of a sample in a microfluidic system of a cassette can be performed by using an analyzer that controls fluid flow in the cassette, and by using feedback from one or more measured signals to modulate fluid flow.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method comprising:
   initiating detection of fluids at a first measurement zone of a microfluidic system;
   detecting a first wash fluid and a second wash fluid at the first measurement zone and forming a first signal corresponding to the first wash fluid and a second signal corresponding to the second wash fluid, wherein the detection step is performed by measuring light transmittance or light absorbance through the first and second wash fluids;
   counting a series of signals generated from detecting a series of wash fluids passing across the first measurement zone, each signal having an intensity above or below a threshold intensity;
   transmitting a first pattern of signals to a control system, the first pattern of signals comprising at least two of:
   a) an intensity of the first signal;
   b) a duration of the first signal;
   c) a position of the first signal in time relative to a second position in time; and
   d) an average time period between the first and the second signals, wherein the intensity of the first signal is indicative of a fluid type and the duration of the first signal is indicative of a volume and/or flow rate of the first fluid; and
   determining whether to modulate fluid flow in the microfluidic system and/or alerting a user of an abnormality in an analysis being conducted in the microfluidic system based at least in part on the number of signals having the intensity above or below the threshold intensity and/or the first pattern of signals.

2. A method as in claim 1, comprising continuously or periodically detecting the passing of any fluids across the first measurement zone.

3. A method as in claim 1, wherein determining whether to modulate fluid flow in the microfluidic system comprises determining whether to stop an analysis being conducted in the microfluidic system.

4. A method as in claim 1, further comprising transmitting an electrical signal from the control system to a component of the microfluidic system that can modulate fluid flow as a result of the transmitting step.

5. A method as in claim 4, wherein the component of the microfluidic system is a pump or a vacuum.

6. A method as in claim 4, wherein the component of the microfluidic system is a valve.

7. A method as in claim 1, further comprising comparing the first pattern of signals to a control pattern of signals or values pre-programmed into the control system.

8. A method as in claim 1, wherein the first pattern of signals comprises an intensity of the first signal, and wherein intensity of the first signal comprises an average or maximum intensity.

9. A method as in claim 1, wherein the first pattern of signals comprises an intensity of the first signal and a duration of the first signal.

10. A method as in claim 1, wherein the first pattern of signals comprises an intensity of the first signal and a position of the first signal in time relative to a time of the initiation step.

11. A method as in claim 1, wherein the first pattern of signals comprises an intensity of the first signal and an average time period between the first and second signals.

12. A method as in claim 1, wherein the first and second fluids are immiscible with one another.

13. A method as in claim 1, wherein the first fluid is a liquid and the second fluid is a gas.

14. A method as in claim 1, wherein the first and second fluids are miscible with one another.

15. A method as in a claim 1, wherein the first and second fluids are separated by a third, immiscible fluid.

16. A method as in claim 1, comprising passing a fluid sample across the first measurement zone.

17. A method as in claim 16, wherein the fluid sample comprises whole blood.

18. A method as in claim 1, comprising alerting a user of an abnormality in an analysis being conducted in the microfluidic system.

19. A method as in claim 18, comprising providing the user with information about the analysis based on detection of an abnormality during the analysis.

20. A method as in claim 19, wherein providing the user with information comprises alerting the user via a user interface.

21. A method as in claim 19, wherein the information provided to the user comprises information that results of the analysis should not be relied upon, that the analysis needs to be performed again, that the analysis may take longer to perform, or that the user should take some action.

22. A method as in claim 19, wherein the information provided to the user comprises information that the analysis is cancelled and/or the results should be disregarded.

23. A method as in claim 19, comprising seeking further input from the user after providing the user with the information.

24. A method as in claim 20, wherein the user interface comprises a screen that is part of a sample analyzer, and wherein the sample analyzer comprises the control system and at least one detector for detecting the first and second fluids at the first measurement zone.

25. A method as in claim 1, comprising measuring light transmittance or light absorbance as a function of time.

26. A method as in claim 1, comprising continuously or periodically detecting the passing of fluids across a second measurement zone of the microfluidic system, wherein the first and second measurement zones are positioned in series with respect to one another.

27. A method as in claim 26, wherein detecting the passing of fluids across the second measurement zone is performed without the use of a label and comprises measuring light transmittance or light absorbance through the first and second fluids at the second measurement zone.

28. A method as in claim 1, wherein at least one signal is indicative of a component deposited from a fluid onto a surface of a channel in the first measurement zone.

29. A method as in claim 1, comprising measuring light transmittance or light absorbance through a sample fluid and a series of wash fluids at the first measurement zone.

30. A method as in claim 1, comprising applying a substantially constant vacuum at an outlet in fluid communication with the first measurement zone during flow of the first and second fluids across the first measurement zone.

31. A method as in claim 1, further comprising detecting a third fluid in the first measurement zone.

32. A method as in claim 31, further comprising detecting a fourth fluid and a fifth fluid in the first measurement zone.

33. A method as in claim 16, wherein the fluid sample is blood, serum, or plasma.

34. A method as in claim 1, wherein the first fluid is air.

35. A method as in claim 1, wherein the first fluid is aqueous.

36. A method as in claim 1, wherein the detection step is performed without the use of a label.

* * * * *

UNITED STATES PATENT AND TRADEMARK OFFICE
CERTIFICATE OF CORRECTION

PATENT NO. : 8,580,569 B2  
APPLICATION NO. : 13/088112  
DATED : November 12, 2013  
INVENTOR(S) : Vincent Linder et al.

Page 1 of 1

It is certified that error appears in the above-identified patent and that said Letters Patent is hereby corrected as shown below:

In the Specification:

At column 6, line 64, please insert a --.-- between the words to read as: --determined. For--;

At column 7, line 7, please insert a --.-- between the words to read as: --determined. The--;

At column 7, line 17, please insert a --.-- between the words to read as: --determined. For--;

At column 15, line 8, please insert a --.-- between the words to read as: --channel. In--;

At column 19, line 30, please insert a --.-- between the words to read as: --channel. In--;

At column 20, line 47, please insert a --.-- between the words to read as: --channel. In--;

At column 22, line 26, please insert a --.-- between the words to read as: --mm. In--;

At column 22, line 29, please insert a --.-- between the words to read as: --mm. In--;

At column 23, line 41, please insert a --.-- between the words to read as: --channel. Non-limiting--;

At column 24, line 41, please replace "5 pL" with --5 µL--;

At column 25, line 35, "ABCAS" should read as: --ABCA5--;

At column 25, line 57, please insert a --.-- between the words to read as: --channel. If--;

At column 31, line 13, please insert a --.-- between the words to read as: --channel. In--;

At column 31, line 34, "AP" should read as: --$\Delta P$--;

At column 31, line 37, "AP" should read as: --$\Delta P$--;

At column 35, line 61, please insert a --.-- between the words to read as: --determined. It--;

At column 44, line 10, please insert a --.-- between the words to read as: --mm. The--;

At column 46, line 2, please insert a --.-- between the words to read as: --channel. Gold--.

Signed and Sealed this  
Twenty-second Day of April, 2014

Michelle K. Lee  
*Deputy Director of the United States Patent and Trademark Office*